(12) United States Patent
Crain et al.

(10) Patent No.: US 6,362,194 B1
(45) Date of Patent: *Mar. 26, 2002

(54) METHOD AND SIMULTANEOUSLY ENHANCING ANALGESIC POTENCY AND ATTENUATING DEPENDENCE LIABILITY CAUSED BY MORPHINE AND OTHER BIMODALLY-ACTING OPIOID AGONISTS

(75) Inventors: Stanley M. Crain, Leonia, NJ (US); Ke-fei Shen, Flushing, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/585,517

(22) Filed: Jun. 1, 2000

Related U.S. Application Data

(63) Continuation of application No. 09/094,977, filed on Jun. 16, 1998, now Pat. No. 6,096,756, which is a continuation of application No. 08/759,590, filed on Dec. 3, 1996, now Pat. No. 5,767,125, which is a continuation-in-part of application No. 08/276,966, filed on Jul. 19, 1994, now Pat. No. 5,512,578, which is a continuation-in-part of application No. 08/097,460, filed on Jul. 27, 1993, now Pat. No. 5,472,943, which is a continuation-in-part of application No. 07/947,690, filed on Sep. 19, 1992, now abandoned.

(51) Int. Cl.$^7$ ............................................. A01N 43/42
(52) U.S. Cl. ..................................................... 514/285
(58) Field of Search ........................................ 514/285

(56) References Cited

U.S. PATENT DOCUMENTS

| | | | |
|---|---|---|---|
| 3,332,950 A | | 7/1967 | Blumberg et al. |
| 4,361,553 A | | 11/1982 | Loh et al. |
| 4,457,933 A | | 7/1984 | Gordon et al. |
| 4,760,069 A | * | 7/1988 | Rezeszotarski et al. ..... 514/285 |
| 4,769,372 A | | 9/1988 | Kreek |
| 4,882,335 A | | 11/1989 | Sinclair |
| 4,889,860 A | * | 12/1989 | Rezeszotarski et al. ..... 514/279 |
| 5,075,341 A | * | 12/1991 | Mendelson et al. .......... 514/279 |
| 5,086,058 A | | 2/1992 | Sinclair |
| 5,096,715 A | | 3/1992 | Sinclair |
| 5,317,022 A | * | 5/1994 | Borsodi et al. .............. 514/282 |
| 5,321,012 A | * | 6/1994 | Mayer et al. .................. 514/25 |
| 5,352,680 A | * | 10/1994 | Portoghese et al. .......... 514/285 |

FOREIGN PATENT DOCUMENTS

| | | | |
|---|---|---|---|
| AU | 85/50585 | | 6/1986 |
| AU | 88/26432 | | 6/1989 |
| AU | 88/18970 | | 1/1990 |
| AU | 92/24023 | | 2/1993 |
| EP | 144243 | | 6/1985 |
| EP | 319243 | | 6/1989 |
| EP | 352361 | | 1/1990 |
| EP | 415693 | | 3/1991 |
| WO | WO87/01703 | | 3/1987 |
| WO | WO94/06426 | | 3/1994 |
| WO | 9406426 | * | 3/1994 ................. 514/285 |
| WO | WO95/03804 | | 2/1995 |
| WO | 9503804 | | 9/1995 |

OTHER PUBLICATIONS

Datta, et al., *Peptides*, vol. 3, pp. 433–437, 1992.
Tremblay, et al., *Psychopharmacology*, vol. 49, pp. 41–48, 1976.
Shen and Crain, *Brain Research*, vol. 636, pp. 286–291, 1994.
Berkow, Robert et al., *The Merck Manual of Diagnosis and Therapy*, 16th Edition, Merck & Co. Inc., NY 1992 pp. 1558–1559.
Reynolds, JEF Martindale, *The Extra Pharmacopoeica*, 30th Ed., The Pharmaceutical Press, London, 1993, pp. 687–688.
Shen and Crain, *Regulatory Peptides*, in press (1993).
Shen and Crain, *Brain Research*, 597:74–83 (1992).
Shen and Crain, *Brain Research*, 575:13–24 (1992).
Wang, et al., *Chinese J. Pharm. Toxicol.*, 6:36–40 (1992) and English translation thereof.
Bo–Yi, Quin, *New Drugs and Clinical Remedies*, 12:119–123 (1992) and English translation thereof.
Lange, et al., *Toxicol. Applied Pharm.*, 54:177–186 (1980).
Terwillinger, et al., *Brain Research*, 548:100–110 (1991).
Shen, et al., *Brain Research*, 559:130–138 (1991).
Crain and Shen, *Trends Pharmacol. Sci.*, 11:77–81 (1990).
Fujimoto, et al., *Neuropharmacol.*, 29:609–617 (1990).
Shen and Crain, *Brain Research*, 531:1–7 (1990).
Shen and Crain, *Brain Research*, 491:227–242 (1989).
North, *Trends Neurosci.*, 9:114–117 (1986).
Magnan, et al., *Nauyn–Schmiedelberg's Arch. Pharmacol.*, 319:197–205 (1982).
Bentley and Hardy, *J. American Chem. Soc.*, 89:3281–3286 (1967).
Bentley and Hardy, *Proc. Chem. Soc.*, p. 220 (1963).
Holmes and Fujimoto, *Anesth. Analg.*, 77:1166–1173 (1993).
Miaskowski and Levine, *Brain Research*, 596:41–45 (1992).
Vaccarino, et al., *Pain*, 36:103–109 (1989).

(List continued on next page.)

Primary Examiner—James H. Reamer
(74) Attorney, Agent, or Firm—Amster, Rothstein & Ebenstein

(57) ABSTRACT

This invention relates to a method for selectively enhancing the analgesic potency of a bimodally-acting opioid agonist such as morphine and simultaneously attenuating anti-analgesia, hyperalgesia, hyperexcitability, physical dependence and/or tolerance effects associated with the administration of the bimodally-acting opioid agonist. The method of the present invention comprises administering to a subject an analgesic or sub-analgesic amount of a bimodally-acting opioid agonist such as morphine and an amount of an excitatory opioid receptor antagonist such as naltrexone or nalmefene effective to enhance the analgesic potency of the bimodally-acting opioid agonist and attenuate the anti-analgesia, hyperalgesia, hyperexcitability, physical dependence and/or tolerance effects of the bimodally-acting opioid agonist.

31 Claims, 12 Drawing Sheets

OTHER PUBLICATIONS

Cappell, et al., *Pharmacology Biochemistry & Behavior*, 34:425–427 (1989).
Gardner, *Substance Abuse*, 2d ed., pp. 70–99 (1992).
Shen and Crain, *Brain Res.*, 636:286–297 (1994).
Greenstein, et al., *Subst. Abuse*, 2d ed., pp. 562–573 (1992).
Gonzales, et al., *Drugs*, 35:193–213 (1988).
Shen and Crain, *J. Neurosci.*, 14:5570–5579 (1994).
Blane, et al., *Brit. J. Pharmacol. Chemother.*, 30:11–22 (1967).
Fujimoto, et al., *J. Pharm. Exp. Ther.*, 251:1045–1052 (1989).
Gillman, et al., *Intern. J. Neurosci.*, 48:321–324 (1989).
Gillman, et al., *J. Neurol. Sciences*, 49:41–49 (1981).
Gillman, et al., *South African J. Science*, 83:560–563 (1987).
Pederson, et al., *Brit. J. Anaesth.*, 57:1045–1046 (1985).
Schmidt, et al., *Anesthesia*, 40:583–586 (1985).
Bergman, et al., *Arch. Int. Pharmacodyn.*, 291:229–237 (1988).
Levine, et al., *J. Clin. Invest.*, 82:1574–1577 (1988).
Crain and Shen, *J. Pharmacol. Exp. Ther.*, 260:182–186 (1992).
Goldberg, et al., *Science*, 166:1548–1549 (1969).
Lasagna, *Proc. Royal Soc. Med.*, 58(11):978–983 (1965).
Taiwo, et al., *J. Pharm. Exp. Therapeutics*, 249:97–100 (1989).
Arts, et al., *Pharm. Biochemistry Behavior*, 46:623–629 (1993).
Horan, et al., *J. Pharm. Exp. Therapeutics*, 265:1446–1454 (1993).
Kayser, et al., *Brain Research*, 371:37–41 (1986).
Takemori, et al., *J. Pharm. Exp. Therapeutics*, 266:121–124 (1993).
Crain, et al., *Brain Research*, 455:99–109 (1988).
Buchsbaum, et al., *Nature*, 270:620–622 (1977).
Levine, *Nature*, 278:740–741 (1979).
Gillman, et al., *European J. Pharmacol.*, 61: 175–177 (1980).
Levine, *Brain Research*, 365:377–378 (1986).
Budd, K., *Ballieres Clin. Anesthesiology*, 1:993–1011 (1987).
Gillman and Lichtigfield, *South African Med. J.*, 70:650–651 (1986).

\* cited by examiner

Morphine
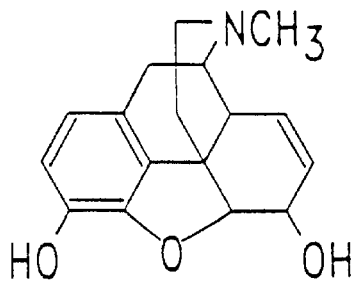
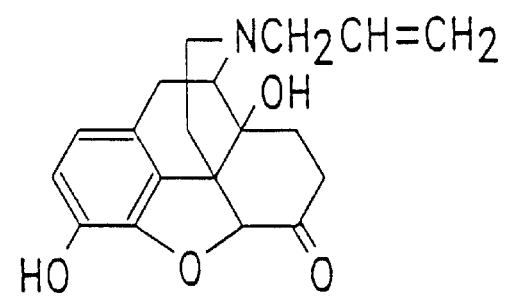
Naloxone
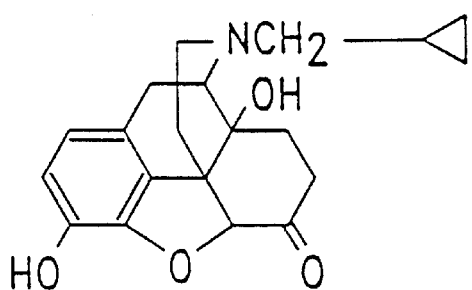
Naltrexone (R=O)
Nalmefene (R=CH$_2$)
FIG. 1

| Acute Test | Alteration of Action Potential Duration (APD) (APD shortening: ↓ ;APD prolongation: ↑ ;No APD change: 0) | | |
|---|---|---|---|
| | Naive DRG Neurons | | Chronic Morphine-Treated Neurons (1uM; >1wk) | Chronic Co-treatment with Mor + Antag. at Excit. Op. Rec. (pM) |
| | Control BSS | BSS + Antag. at Excit.Op.Rec. (pM) | After Washout with BSS | |
| 1 – 10 uM morphine | ↓ (inhibitory) ("analgesia") | ↓↓ | ↑ ("tolerance") | ↓ |
| pM – nM morphine | ↑ ("excitatory antianalgesia") | ↓ (unmasking of inhibitory effects) | ↓ | ↓ |
| ~ fM morphine or dyn A-(1–13) | 0 | 0 | ↑ (excitatory supersensitivity) | 0 |
| nM naloxone | 0 | 0 | ↑ ("dependence") ("withdrawal effect") | 0 |

FIG. 6

METHOD AND SIMULTANEOUSLY ENHANCING ANALGESIC POTENCY AND ATTENUATING DEPENDENCE LIABILITY CAUSED BY MORPHINE AND OTHER BIMODALLY-ACTING OPIOID AGONISTS

CROSS-REFERENCE TO RELATED APPLICATIONS

This is a continuation of application Ser. No. 09/094,977, filed Jun. 16, 1998, now U.S. Pat. No. 6,096,756, which is a continuation of application Ser. No. 08/759,590, filed Dec. 3, 1996, now U.S. Pat. No. 5,767,125, which is a continuation-in-part of application Ser. No. 08/276,966, filed Jul. 19, 1994, which issued as U.S. Pat. No. 5,512,578 and reissued as U.S. Reissue Pat. No. 36,547, which is a continuation-in-part of application Ser. No. 08/097,460, filed Jul. 27, 1993, now U.S. Pat. No. 5,472,943, which is a continuation-in-part of application Ser. No. 07/947,690, filed Sep. 19, 1992, now abandoned, the contents of which are hereby incorporated by reference in their entirety.

FIELD OF THE INVENTION

This invention relates to a method of enhancing the analgesic (inhibitory) effects of bimodally-acting opioid agonists, including morphine, codeine and other-clinically used opioid analgesics, while at the same time attenuating anti-analgesia, physical dependence, tolerance, hyperexcitability, hyperalgesia, and other undesirable (excitatory) side effects typically caused by chronic use of bimodally-acting opioid agonists.

"Bimodally-acting opioid agonists" are opioid agonists that bind to and activate both inhibitory and excitatory opioid receptors on nociceptive neurons which mediate pain. Opioid analgesia results from activation by opioid agonists of inhibitory opioid receptors on neurons in the nociceptive (pain) pathways of the peripheral and central nervous systems. The undesirable side effects, including anti-analgesic actions, hyperexcitability and hyperalgesia, the development of physical dependence, and some types of tolerance result from sustained activation by bimodally-acting opioid agonists of excitatory opioid receptors on neurons in the nociceptive (pain) pathways of the peripheral and central nervous systems.

In the instant invention, a very low dose of a selective excitatory opioid receptor antagonist, an opioid which binds to and acts as an antagonist to excitatory but not inhibitory opioid receptors on nociceptive neurons which mediate pain, is combined with a dose of a bimodally-acting opioid agonist so as to enhance the degree of analgesia (inhibitory effects) and attenuate the undesired side effects (excitatory effects).

BACKGROUND OF THE INVENTION

Morphine or other bimodally-acting opioid agonists are administered to relieve severe pain due to the fact that they have analgesic effects mediated by their activation of inhibitory opioid receptors on nociceptive neurons (see North, *Trends Neurosci.*, Vol. 9, pp. 114–117 (1986) and Crain and Shen, *Trends Pharmacol. Sci.*, Vol. 11, pp. 77–81 (1990)).

However, morphine and other bimodally-acting opioid agonists also activate opioid excitatory receptors on nociceptive neurons, which attenuate the analgesic potency of the opioids and result in the development of physical dependence and increased tolerance (see Shen and Crain, *Brain Res.*, Vol. 597, pp. 74–83 (1992)), as well as hyperexcitability, hyperalgesia and other undesirable (excitatory) side effects. As a result, a long-standing need has existed to develop a method of both enhancing the analgesic (inhibitory) effects of bimodally-acting opioid agonists and blocking or preventing undesirable (excitatory) side effects caused by such opioid agonists. The present invention satisfies this need.

SUMMARY OF THE INVENTION

This present invention is directed to a method for selectively enhancing the analgesic potency of a bimodally-acting opioid agonist and simultaneously attenuating anti-analgesia, hyperalgesia, hyperexcitability, physical dependence and/or tolerance effects associated with the administration of the bimodally-acting opioid agonist. The method comprises administering to a subject an analgesic or sub-analgesic amount of a bimodally-acting opioid agonist and an amount of an excitatory opioid receptor antagonist effective to enhance the analgesic potency of the bimodally-acting opioid agonist and attenuate the anti-analgesia, hyperalgesia, hyperexcitability, physical dependence and/or tolerance effects of the bimodally-acting opioid agonist.

The present invention also provides a method for treating pain in a subject comprising administering to the subject an analgesic or sub-analgesic amount of a bimodally-acting opioid agonist and an amount of an excitatory opioid receptor antagonist effective to enhance the analgesic potency of the bimodally-acting opioid agonist and attenuate anti-analgesia, hyperalgesia, hyperexcitability, physical dependence and/or tolerance-effects of the bimodally-acting opioid agonist.

The present invention further provides a method for treating an opiate addict comprising administering to the opiate addict an amount of an excitatory opioid receptor antagonist either alone or in combination with a bimodally-acting opioid agonist effective to attenuate physical dependence caused by a bimodally-acting opioid agonist and enhance the analgesic potency of a bimodally-acting opioid agonist.

Finally, the present invention provides a composition comprising an analgesic or sub-analgesic amount of a bimodally-acting opioid agonist and an amount of an excitatory opioid receptor antagonist effective to enhance the analgesic potency of the bimodally-acting opioid agonist and attenuate the anti-analgesia, hyperalgesia, hyperexcitability, physical dependence and/or tolerance effects of the bimodally-acting opioid agonist in a subject administered the composition.

BRIEF DESCRIPTION OF THE FIGURES

FIG. 1 represents the structural formulae of the bimodally-acting opioid agonist morphine and the excitatory opioid receptor antagonists naloxone, naltrexone and nalmefene. Naltrexone is the N-cyclopropylmethyl congener of naloxone. Nalmefene is the 6-methylene derivative of naltrexone (Hahn, E. F., et al. *J. Med. Chem.* 18:259–262 (1975)).

FIG. 6 represents the assay procedure used to demonstrate that selective antagonists at excitatory opioid receptors prevents development of tolerance/dependence during chronic co-treatment of DRG neurons with morphine.

DETAILED DESCRIPTION OF THE INVENTION

Figure 2A:
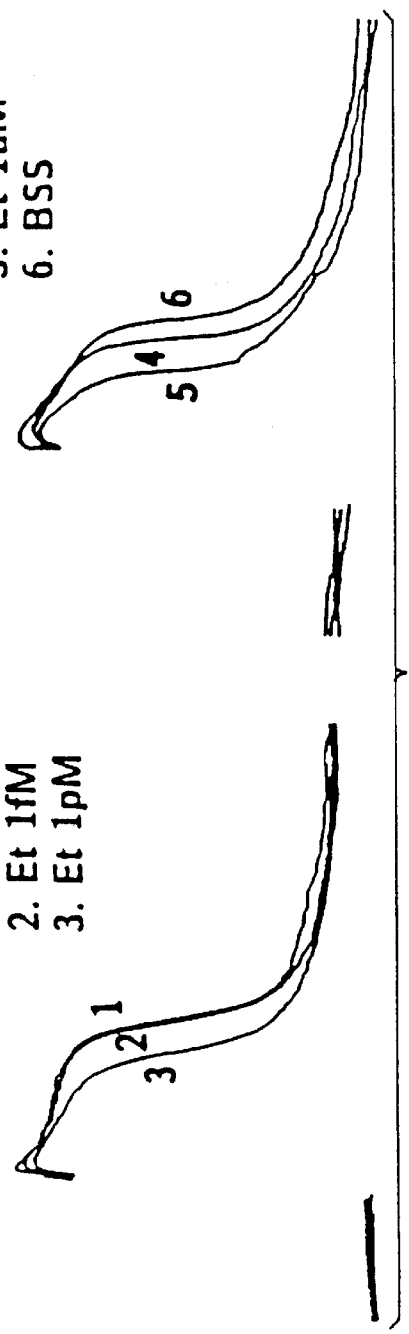
FIG. 2 represents the direct inhibitory effect of etorphine on the action potential duration (APD) of nociceptive types of sensory neurons and the blocking effect of etorphine on the excitatory response (APD prolongation) elicited by morphine. Acute application of low (pM-nM) concentrations of etorphine to naive dorsal root ganglion (DRG) neurons elicits dose-dependent, naloxone-reversible inhibitory shortening of the APD. In contrast, morphine and other bimodally-acting opioid agonists elicit excitatory APD prolongation at these low concentrations which can be selectively blocked by <pM levels of etorphine, resulting in unmasking of potent inhibitory APD shortening by nM morphine.

As used herein, the term "opioid" refers to compounds which bind to specific opioid receptors and have agonist (activation) or antagonist (inactivation) effects at these receptors, such as opioid alkaloids, including the agonist morphine and the antagonist naloxone, and opioid peptides, including enkephalins, dynorphins and endorphins. The term "opiate" refers to drugs derived from opium or related analogs.

"Bimodally-acting opioid agonists" are opioid agonists that bind to and activate both inhibitory and excitatory opioid receptors on nociceptive neurons which mediate pain. Activation of inhibitory receptors by said agonists causes analgesia. Activation of excitatory receptors by said agonists results in anti-analgesia, hyperexcitability, hyperalgesia, as well as development of physical dependence, tolerance and other undesirable side effects.

Bimodally-acting opioid agonists suitable for use in the present invention may be identified by measuring the opioid's effect on the action potential duration (APD) of dorsal root ganglion (DRG) neurons in tissue cultures. In this regard, bimodally-acting opioid agonists are compounds which elicit prolongation of the APD of DRG neurons at pM-nM concentrations (i.e. excitatory effects), and shortening of the APD of DRG neurons at $\mu$M concentrations (i.e. inhibitory effects). Suitable bimodally-acting opioid agonists include but are not limited to morphine, codeine, fentanyl analogs, pentazocine, buprenorphine, methadone, enkephalins, dynorphins, endorphins and similarly acting opioid alkaloids and opioid peptides. For purposes of treating pain, morphine and codeine are preferred. Buprenorphine and methadone are preferred for treating opioid addiction.

"Excitatory opioid receptor antagonists" are opioids which bind to and act as antagonists to excitatory but not inhibitory opioid receptors on nociceptive neurons which mediate pain. That is, excitatory opioid receptor antagonists are compounds which bind to excitatory opioid receptors and selectively block excitatory opioid receptor functions of nociceptive types of DRG neurons at 1,000 to 10,000-fold lower concentrations than are required to block inhibitory opioid receptor functions in these neurons.

Excitatory opioid receptor antagonists suitable for use in the present invention may also be identified by measuring their effect on the action potential duration (APD) of dorsal root ganglion (DRG) neurons in tissue cultures. In this regard, excitatory opioid receptor antagonists are compounds which selectively block prolongation of the APD of DRG neurons (i.e. excitatory effects) but not the shortening of the APD of DRG neurons (i.e. inhibitory effects) elicited by a bimodally-acting opioid receptor agonist. Suitable excitatory opioid receptor antagonists of the invention include nalmefene, naltrexone, naloxone, etorphine and dihydroetorphine, as well as similarly acting opioid alkaloids and opioid peptides. Preferred excitatory opioid receptor antagonists are nalmefene and naltrexone because of their longer duration of action as compared to naloxone and their greater bioavailability after oral administration.

The bimodally-acting opioid agonists and the excitatory opioid receptor antagonists for use in the present invention may in the form of free bases or pharmaceutically acceptable acid addition salts thereof. Examples of suitable acids for salt formation include but are not limited to methanesulfonic, sulfuric, hydrochloric, glucuronic, phosphoric, acetic, citric, lactic, ascorbic, maleic, and the like.

The excitatory opioid receptor antagonist alone, or in combination with the bimodally-acting opioid agonist, may be administered to a human or animal subject by known procedures including but not limited to oral, sublingual, intramuscular, subcutaneous, intravenous, and transdermal modes of administration. When a combination of these compounds are administered, they may be administered together in the same composition, or may be administered in separate compositions. If the bimodally-acting opioid agonist and the excitatory opioid receptor antagonist are administered in separate compositions, they may be administered by similar or different modes of administration, and may be administered simultaneously with one another, or shortly before-or after the other.

The bimodally-acting opioid agonists and the excitatory opioid receptor antagonists may be formulated in compositions with a pharmaceutically acceptable carrier. The carrier must be "acceptable" in the sense of being compatible with the other ingredients of the formulation and not deleterious to the recipient thereof. Examples of suitable pharmaceutical carriers include lactose, sucrose, starch, talc, magnesium stearate, crystalline cellulose, methyl cellulose, carboxymethyl cellulose, glycerin, sodium alginate, gum arabic, powders, saline, water, among others. The formulations may conveniently be presented in unit dosage and may be prepared by methods well-known in the pharmaceutical art, by bringing the active compound into association with a carrier or diluent, as a suspension or solution, and optionally one or more accessory ingredients, e.g. buffers, flavoring agents, surface active agents, and the like. The choice of carrier will depend upon the route of administration.

For oral and sublingual administration, the formulation may be presented as capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate.

For intravenous, intramuscular, or subcutaneous administration, the compounds may combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

For transdermal administration, the compounds may be combined with skin penetration enhancers such as propylene glycol, polyethylene glycol, isopropanol, ethanol, oleic acid, N-methylpyrrolidone, and the like, which increase the permeability of the skin to the compounds, and permit the compounds to penetrate through the skin and into the bloodstream. The compound/enhancer compositions also may be combined additionally with a polymeric substance such as ethylcellulose, hydroxypropyl cellulose, ethylene/vinylacetate, polyvinyl pyrrolidone, and the like, to provide the composition in gel form, which can be dissolved in solvent such as methylene chloride, evaporated to the desired viscosity, and then applied to backing material to provide a patch.

When the excitatory opioid receptor antagonist is used in combination with the bimodally-acting opioid agonist, the amount of the bimodally-acting opioid agonist administered may be an analgesic or sub-analgesic amount. As used herein, an "analgesic" amount is amount of the bimodally-acting opioid agonist which causes analgesia in a subject administered the bimodally-acting opioid agonist alone, and includes standard doses of the agonist which are typically administered to cause analgesia (e.g, mg doses). A "sub-analgesic" amount is an amount which does not cause analgesia in a subject administered the bimodally-acting opioid agonist alone, but when used in combination with the excitatory opioid receptor antagonist, results in analgesia. The amount of the excitatory opioid receptor antagonist is an amount effective to enhance the analgesic potency of the bimodally-acting opioid agonist and attenuate the anti-analgesia, hyperalgesia, hyperexcitability, physical dependence and/or tolerance effects of the bimodally-acting opioid agonist. Based on studies of nociceptive DRG neurons in culture and in vivo mouse studies, the amount of the excitatory opioid receptor administered may be between about 1000 and about 10,000,000 fold less, and preferably between about 10,000 and 1,000,000 fold less than the amount of the bimodally-acting opioid agonist administered. The optimum amounts of the bimodally-acting opioid agonist and the excitatory opioid receptor antagonist administered will of course depend upon the particular agonist and antagonist used, the carrier chosen, the route of administration, and the pharmacokinetic properties of the subject being treated.

When the excitatory opioid receptor antagonist is administered alone (i.e. for treating an opioid addict), the amount of the excitatory opioid receptor antagonist administered is an amount effective to attenuate physical dependence caused by a bimodally-acting opioid agonist such as morphine and enhance the analgesic potency of the bimodally-acting opioid agonist. That is, the amount of the excitatory opioid receptor antagonist is an amount which blocks the excitatory effects (i.e. physical dependence) of the bimodally-acting opioid agonist without blocking the inhibitory effects (i.e. analgesic effects) of the bimodally-acting opioid agonist. This amount is readily determinable by one skilled in the art.

The present invention is described in the following examples which are set forth to aid in the understanding of the invention, and should not be construed to limit in any way the invention as defined in the claims which follow thereafter.

EXAMPLE 1

Etorphine and Dihydroetorphine Act as Potent Selective Antagonists at Excitatory Opioid Receptors on DRG Neurons Thereby Enhancing Inhibitory Effects of Bimodally-Acting Opioid Agonists Methods The experiments described herein were carried out on dorsal root ganglion (DRG) neurons in organotypic explants of spinal cord with attached DRGs from 13-day-old fetal mice after 3 to 5 weeks of maturation in culture. The DRG-cord explants were grown on collagen-coated coverslips in Maximow depression-slide chambers. The culture medium consisted of 65% Eagle's minimal essential medium, 25% fetal bovine serum, 10% chick embryo extract, 2 mM glutamine and 0.6% glucose. During the first week in vitro the medium was supplemented with nerve growth factor (NGF-7S) at a concentration of about 0.5 µg/ml, to enhance survival and growth of the fetal mouse DRG neurons.

In order to perform electrophysiologic procedures, the culture coverslip was transferred to a recording chamber containing about 1 ml of Hanks' balanced salt solution (BSS). The bath solution was supplemented with 4 mM $Ca^{2+}$ and 5 mM $Ba^{2+}$ (i.e., Ca, Ba/BSS) to provide a prominent baseline response for pharmacological tests. Intracellular recordings were obtained from DRG perikarya selected at random within the ganglion. The micropipettes were filled with 3 M KCl (having a resistance of about 60–100 megohms) and were connected via a chloridized silver wire to a neutralized input capacity preamplifier (Axoclamp 2A) for current-clamp recording. After impalement of a DRG neuron, brief (2 msec) depolarizing current pulses were applied via the recording electrode to evoke action potentials at a frequency of 0.1 Hz. Recordings of the action potentials were stored on a floppy disc using the P-clamp program (Axon Instruments) in a microcomputer (IBM AT-compatible).

Drugs were applied by bath perfusion with a manually operated, push-pull syringe system at a rate of 2–3 ml/min. Perfusion of test agents was begun after the action potential and the resting potential of the neuron reached a stable condition during >4 minute pretest periods in control Ca, Ba/BSS. Opioid-mediated changes in the APD were considered significant if the APD alteration was >10% of the control value for the same cell and was maintained for the entire test period of 5 minutes. The APD was measured as the time between the peak of the APD and the inflection point on the repolarizing phase. The following drugs were used in this and the following Examples: etorphine, diprenorphine and morphine (gifts from Dr. Eric Simon); dihydroetorphine (gift from Dr. B.-Y. Qin, China and United Biomedical, Inc.); naloxone (Endo Labs); naltrexone, DADLE, dynorphin and other opioid peptides (Sigma).

Opioid alkaloids and peptides were generally prepared as 1 mM solutions in $H_2O$ and then carefully diluted with BSS to the desired concentrations, systematically discarding pipette tips after each successive 1–10 or 1–100 dilution step to ensure accuracy of extremely low (fM-pM) concentrations.

Results

Intracellular recordings were made from small- and medium-size DRG neuron perikarya (about 10–30 µm in diameter) which generate relatively long APDs (greater than 3 msec in Ca/Ba BSS) and which show characteristic responsiveness to opioid agonists and other properties of primary afferent nociceptive neurons as occur in vivo. Acute application of selective inhibitory opioid receptor agonists, e.g., etorphine, to these DRG neurons shortens the APD in 80–90% of the cells tested, whereas low concentrations of bimodally-acting (excitatory/inhibitory) opioids, e.g., morphine, dynorphin, enkephalins, prolong the APD in these same cells. Relatively small numbers of large DRG neurons (about 30–50 µm in diameter) survive in DRG-cord explants (about 10–20%) and show much shorter APDs (about 1–2 msec in Ca/Ba BSS), with no clear-cut inflection or "hump" on the falling phase of the spike. The APD of these large DRG neurons is not altered by exogenous opioids.

The opioid responsiveness of DRG neurons was analyzed by measuring the opioid-induced alterations in the APD of DRG perikarya. A total of 64 DRG neurons, (from 23 DRG-cord explants) were studied for sensitivity to progressive increases in the concentration of etorphine (n=30) or dihydroetorphine (n=38). Etorphine rapidly and dose-dependently shortened the APD in progressively larger fractions of DRG cells at concentrations from 1 fM (30% of cells; n=26) to 1 uM (80% of cells; n=16) (see FIGS. 2 and 3).

Figure 2B:
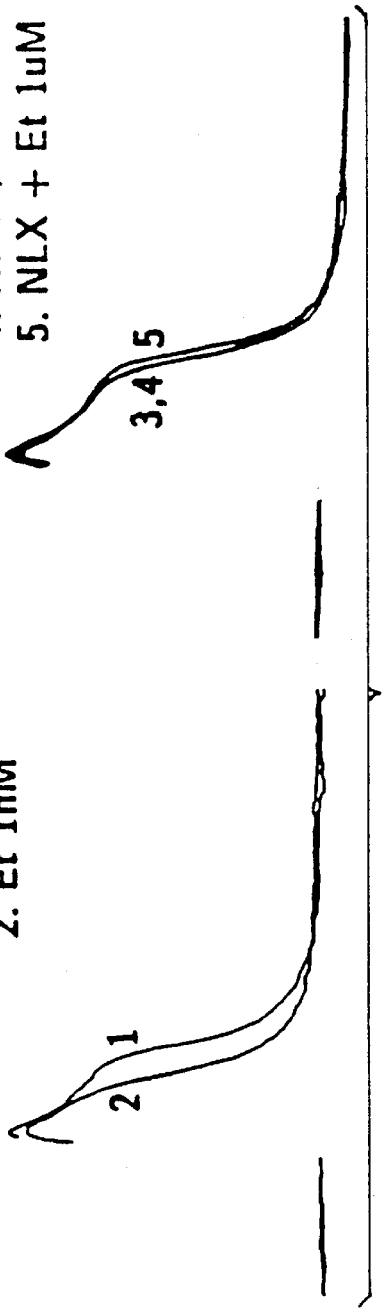

FIG. 2 shows that acute application of low (pM-nM) concentrations of etorphine to naive DRG neurons elicits dose-dependent, naloxone-reversible inhibitory shortening of the action potential duration (APD). In contrast, dynorphin (and many other bimodally-acting opioid agonists, e.g., morphine, DADLE) elicit excitatory APD prolongation at these low concentrations (see FIG. 3), which can be selectively blocked by <pM levels of etorphine, as well as by diprenorphine or naltrexone (see FIGS. 4 and 5). FIG. 2A record 1 shows the action potential (AP) generated by a DRG neuron in balanced salt solution containing 5 mM $Ca^{2+}$ and 5 mM $Ba^{2+}$ (BSS). AP response in this record (and in all records below) is evoked by a brief (2 msec) intracellular depolarizing current pulse. FIG. 2A records 2–5 show that APD is not altered by bath perfusion with 1 fM etorphine (Et) but is progressively shortened in 1 pM, 1 nM and 1 µM concentrations (5 minute test periods). FIG. 2A record 6 shows that APD returns to control value after transfer to BSS (9 minute test). FIG. 2B records 1 and 2 show that APD of another DRG neuron is shortened by application of 1 nM etorphine (2 minute test). FIG. 2B record 3 shows that APD returns to control value after transfer to 10 nM naloxone (NLX). FIG. 2B records 4 and 5 show that APD is no longer shortened by 1 nM or even 1 µM etorphine when co-perfused with 10 nM naloxone (5 minute test periods).

Figure 2C:
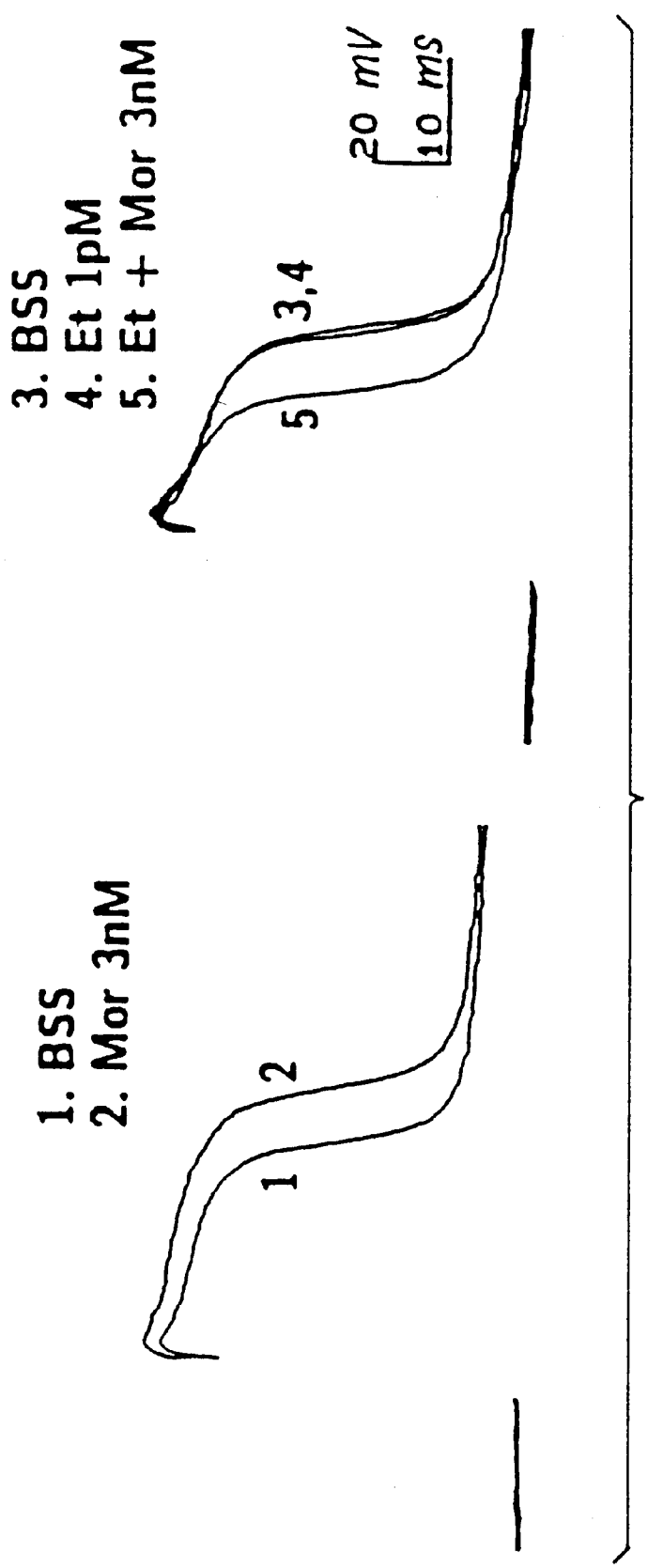

FIG. 2C records 1 and 2 show that APD of another DRG neuron is prolonged by application of 3 nM morphine. FIG. 2C record 3 shows that APD returns to controL value by 5 minutes after washout. FIG. 2C record 4 shows that application of 1 pM etorphine does not alter the APD. FIG. 2C record 5 shows that APD is no longer prolonged by 3 nM morphine when co-perfused with 1 pM etorphine and instead is markedly shortened to a degree which would require a much higher morphine concentration in the absence of etorphine. Similar. results were obtained by pretreatment with 1 pM diprenorphine (see FIG. 4), with 1 pM naltrexone (FIG. 5) or 1 pM naloxone. Records in this and subsequent Figures are from DRG neurons in organotypic DRG-spinal cord explants maintained for 3–4 weeks in culture.

Figure 3:
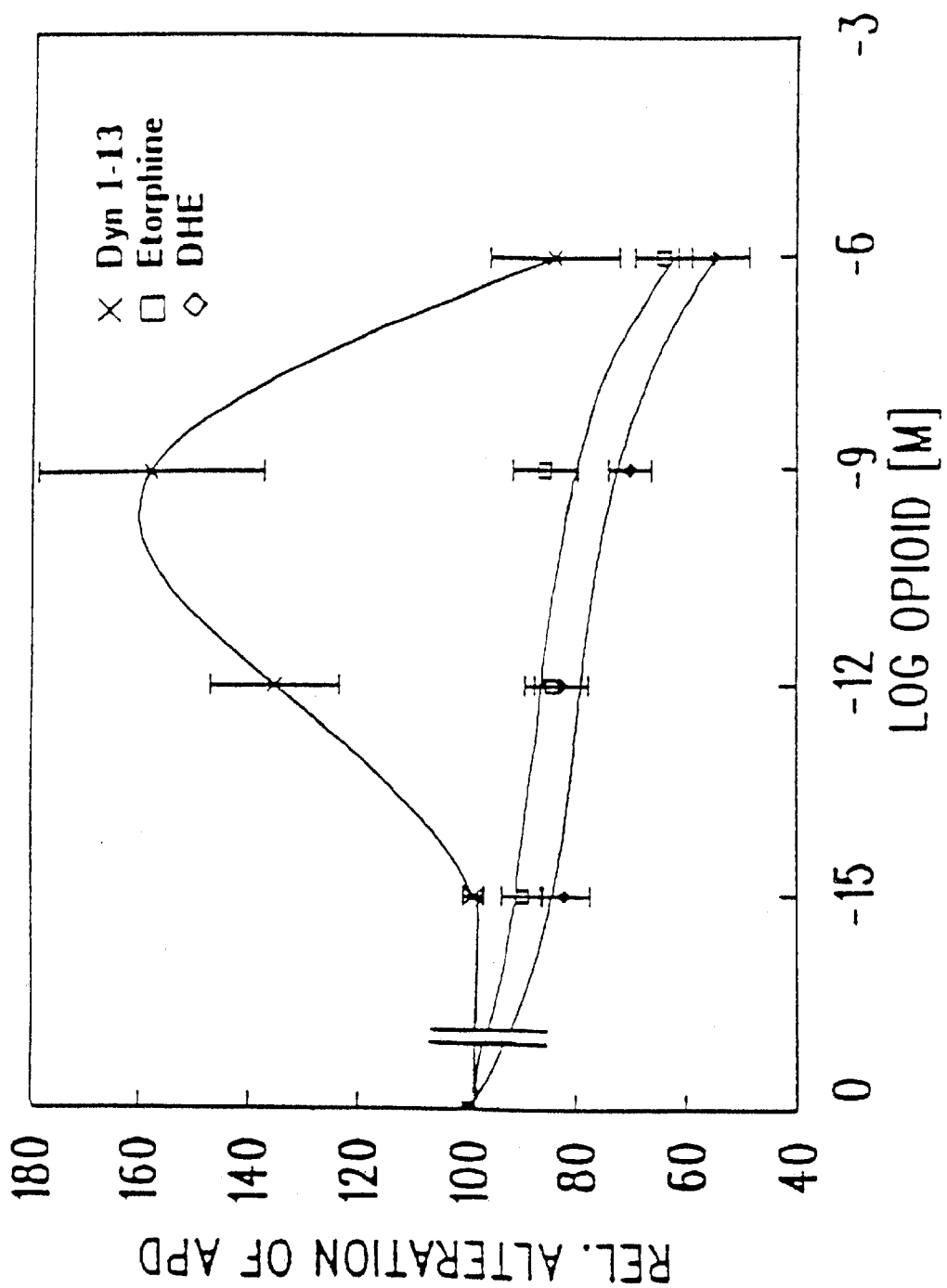
FIG. 3 represents dose-response curves of different opioids, showing that etorphine and dihydroetorphine elicit only inhibitory dose-dependent shortening of the APD of DRG neurons at all concentrations tested (fM-$\mu$M). In contrast, dynorphin A (as well as morphine and other bimodally-acting opioids) elicit dose-dependent excitatory APD prolongation at low concentrations (fM-nM) and requires much higher concentrations (about 0.1–1 $\mu$M) to shorten the APD, thereby resulting in a bell-shaped, dose-response curve.

FIG. 3 shows dose-response curves demonstrating that etorphine (Et) (□) and dihydroetorphine (DHE) (◊) elicit only inhibitory dose-dependent shortening of the APD of DRG neurons at all concentrations tested (fX-µM). In contrast, dynorphin A (1–13) (Dyn) (×) (as well as morphine and other bimodally-acting opioids) elicits dose-dependent excitatory APD prolongation at low concentrations (fM-nM) and generally requires much higher concentrations (about 0.1–1 µM) to shorten the APD, thereby resulting in a bell-shaped dose-response curve. Data were obtained from 11 neurons for the etorphine tests, 13 for the DHE tests and 35 for the dynorphin tests; 5, 8 and 9 neurons were tested (as in FIG. 2) with all four concentrations of etorphine, DHE and dynorphin, respectively (from fM to µM). For sequential dose-response data on the same neuron, the lowest concentrations (e.g., 1 fM) were applied first.

Dihydroetorphine was even more effective (n=38; FIG. 3). Naloxone (10 nM) prevented the etorphine- and dihydroetorphine-induced APD shortening which was previously elicited in the same cells (n=12; FIG. 2B). These potent inhibitory effects of etorphine and dihydroetorphine on DRG neurons at low concentrations are in sharp contrast to the excitatory APD-prolonging effects observed in similar tests with morphine and a wide variety of mu, delta and kappa opioids. None of the DRG neurons tested with different concentrations of etorphine or dihydroetorphine showed prominent APD prolongation.

The absence of excitatory APD-prolonging effects of etorphine and dihydroetorphine on DRG neurons could be due to low binding affinity of these opioid agonists to excitatory opioid receptors. Alternatively, these opioids might bind strongly to excitatory receptors, but fail to activate them, thereby functioning as antagonists. In order to distinguish between these two modes of action, DRG neurons were pretreated with etorphine at low concentrations (fM-pM) that evoked little or no alteration of the APD. subsequent addition of nM concentrations of morphine, DAGO, DADLE or dynorphin to etorphine-treated cells no longer evoked the usual APD prolongation observed in the same cells prior to exposure to etorphine (n=11; see FIG. 2C). This etorphine-induced blockade of opioid excitatory effects on DRG neurons was often effective for periods up to 0.5–2 hours after washout (n=4).

These results demonstrate that etorphine, which has been considered to be a "universal" agonist at mu, delta and kappa opioid receptors (see Magnan et al., *Naunyn-Schmiedeberg's Arch. Pharmacol.*, Vol. 319, pp. 197–205 (1982)), has potent antagonist actions at mu, delta and kappa excitatory opioid receptors on DRG neurons, in addition to its well-known agonist effects at inhibitory opioid receptors. Pretreatment with dihydroetorphine (fM-pM) showed similar antagonist action at excitatory opioid receptor mediating nM opioid-induced APD prolongation (n=2). Furthermore, after selective blockade of opioid excitatory APD-prolonging effects by pretreating DRG neurons with low concentrations of etorphine (fM-pM), which showed little or no alteration of the APD, fM-nM levels of bimodally-acting opioids now showed potent inhibitory APD-shortening effects (5 out of 9 cells) (see FIG. 2C and FIG. 4). This is presumably due to unmasking of inhibitory opioid receptor-mediated functions in these cells after selective blockade of their excitatory opioid receptor functions by etorphine.

EXAMPLE 2
Diprenorphine, Naloxone and Naltrexone, at Low Concentrations, Also Show Potent Selective Antagonist Action at Excitatory opioid Receptors
Drug Tests Mouse DRG-cord explants, grown for >3 weeks as described in Example 1, were tested with the opioid antagonists diprenorphine, naltrexone and naloxone. Electrophysiological recordings were made as in Example 1.
Results The opioid receptor antagonists naloxone and diprenorphine were previously shown to black, at nM concentrations, both inhibitory APD shortening of DRG neurons by $\mu$M opioid agonists as well as excitatory APD prolongation by nM opioids. Tests at lower concentrations have revealed that pM diprenorphine, as well as pM naloxone or naltrexone, act selectively as antagonists at mu, delta and kappa excitatory opioid receptors, comparable to the antagonist effects of pM etorphine and dihydroetorphine. In the presence of pM diprenorphine, morphine (n=7) and DAGO (n=7). no longer elicited APD prolongation at low (pM-nM) concentrations (see FIG. 4A). Instead, they showed progressive dose-dependent APD shortening throughout the entire range of concentrations from fM to $\mu$M (see FIG. 4B), comparable to the dose-response curves for etorphine and dihydroetorphine (see FIG. 3 and FIG. 2C). This unmasking of inhibitory opioid receptor-mediated ADP-shortening effects by pM diprenorphine occurred even in the presence of 10-fold higher concentrations of morphine (see FIG. 4A, records 11 vs. 5).

Figure 4A:
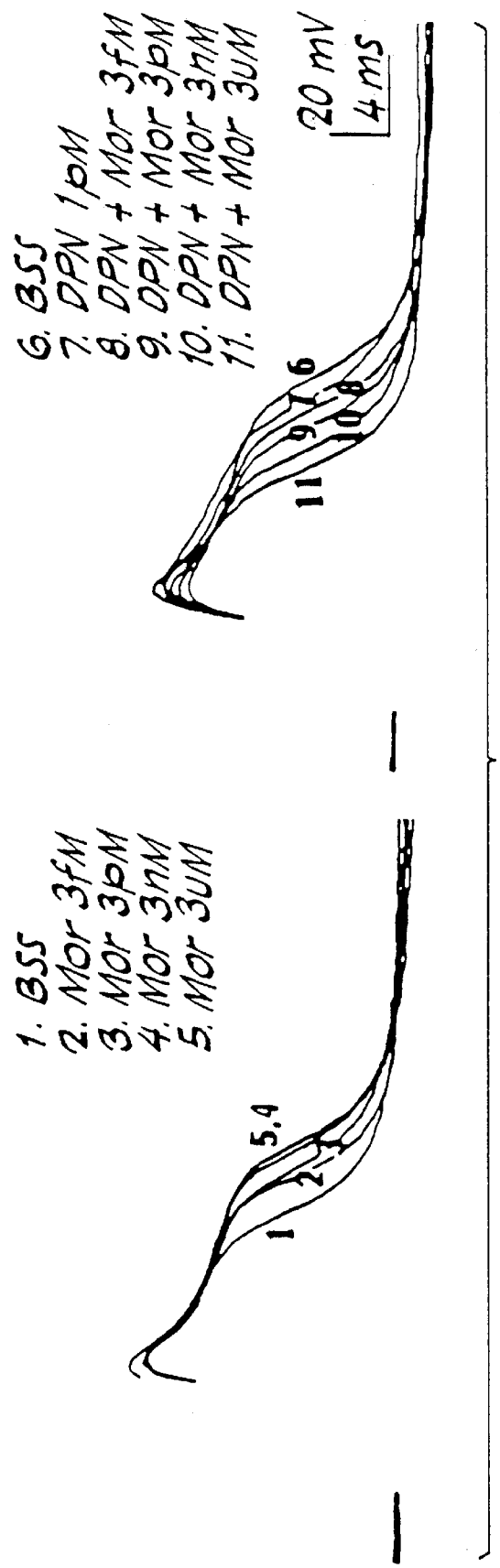
FIGS. 4A and 4B represent the selective blocking of excitatory APD-prolonging effects elicited by morphine in DRG neurons by co-administration of a low (pM) concentration of diprenorphine, thereby unmasking potent dose-dependent inhibitory APD shortening by low concentrations of morphine (comparable to the inhibitory potency of etorphine). In contrast, co-treatment with a higher (nM) concentration of DPN blocks both inhibitory as well as excitatory opioid effects.
Figure 4B:
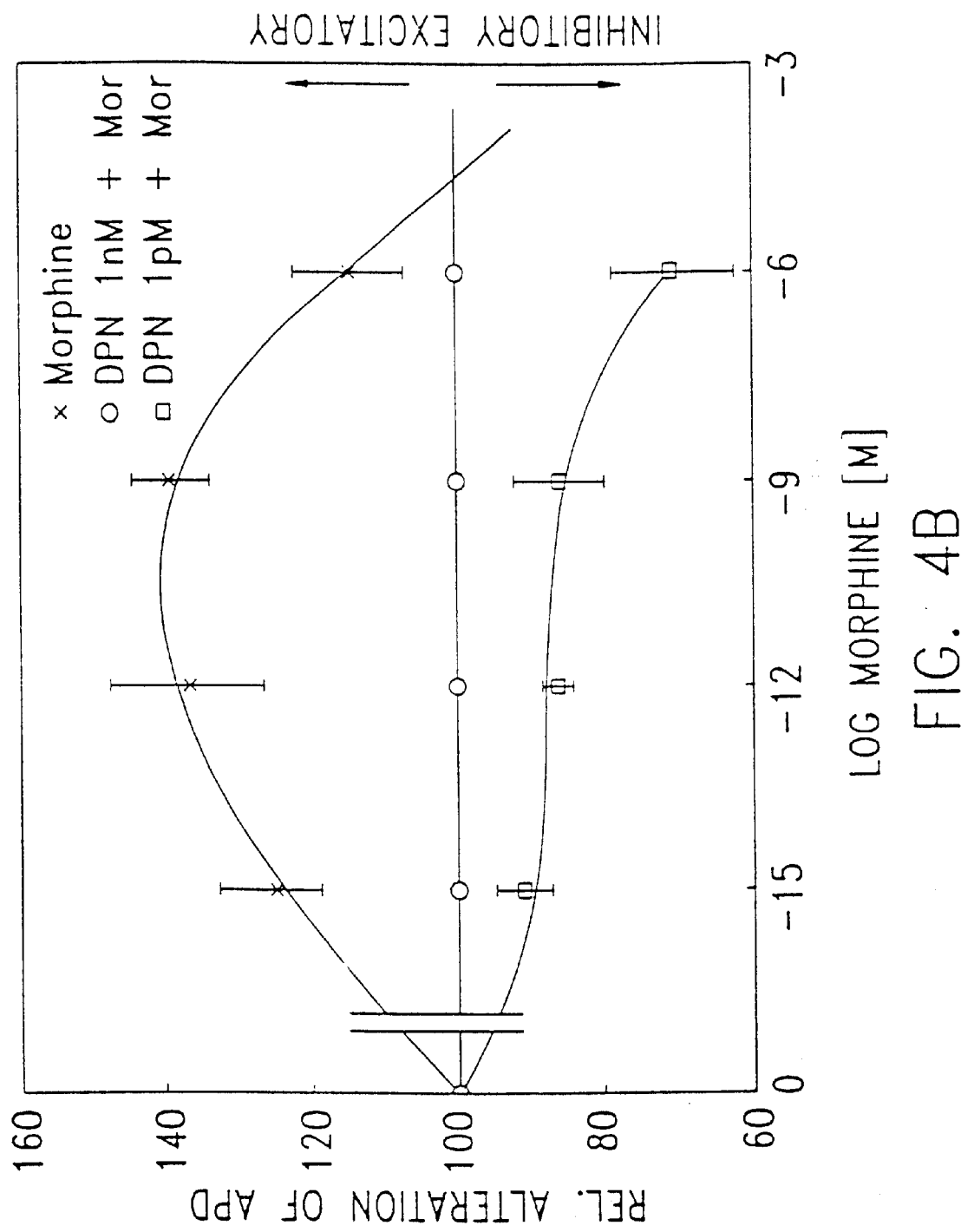

FIG. 4 shows that excitatory APD-prolonging effects elicited by morphine in DRG neurons are selectively blocked by co-administration of a low (pM) concentration of diprenorphine, thereby unmasking potent dose-dependent inhibitory APD shortening by low concentrations of morphine. FIG. 4A records 1–4 show that APD of a DRG neuron is progressively prolonged by sequential bath perfusions with 3 fM, 3 pM and 3 $\mu$M morphine (Mor). FIG. 4A record 5 shows that APD of this cell is only slightly shortened after increasing morphine concentration to 3 pM. FIG. 4A records 6 and 7 show that after transfer to 355, the APD is slightly shortened during pretreatment for 17 minutes with 1 pM diprenorphine (DPN). FIG. 4A records 8–11 show that after the APD reached a stable value in DPN, sequential applications of 3 fM, 3 pM, 3 nM and 3 $\mu$M Mor progressively shorten the APD, in contrast to the marked APD prolongation evoked by these same concentrations of Mor in the absence of DPN (see also FIG. 2C). FIG. 4B dose-response curves demonstrate similar unmasking by 1 pM DPN of potent dose-dependent inhibitory APD shortening by morphine (□) in a group of DRG neurons (n=7), all of which showed only excitatory APD prolongation responses when tested prior to introduction of DPN (X). Note that the inhibitory potency of morphine in the presence of pM DPN becomes comparable to that of etorphine and dihydroetorphine (see FIG. 3). In contrast, pretreatment with a higher (nM) concentration of DPN blocks both inhibitory as well-as excitatory effects of morphine (●).

Figure 5:
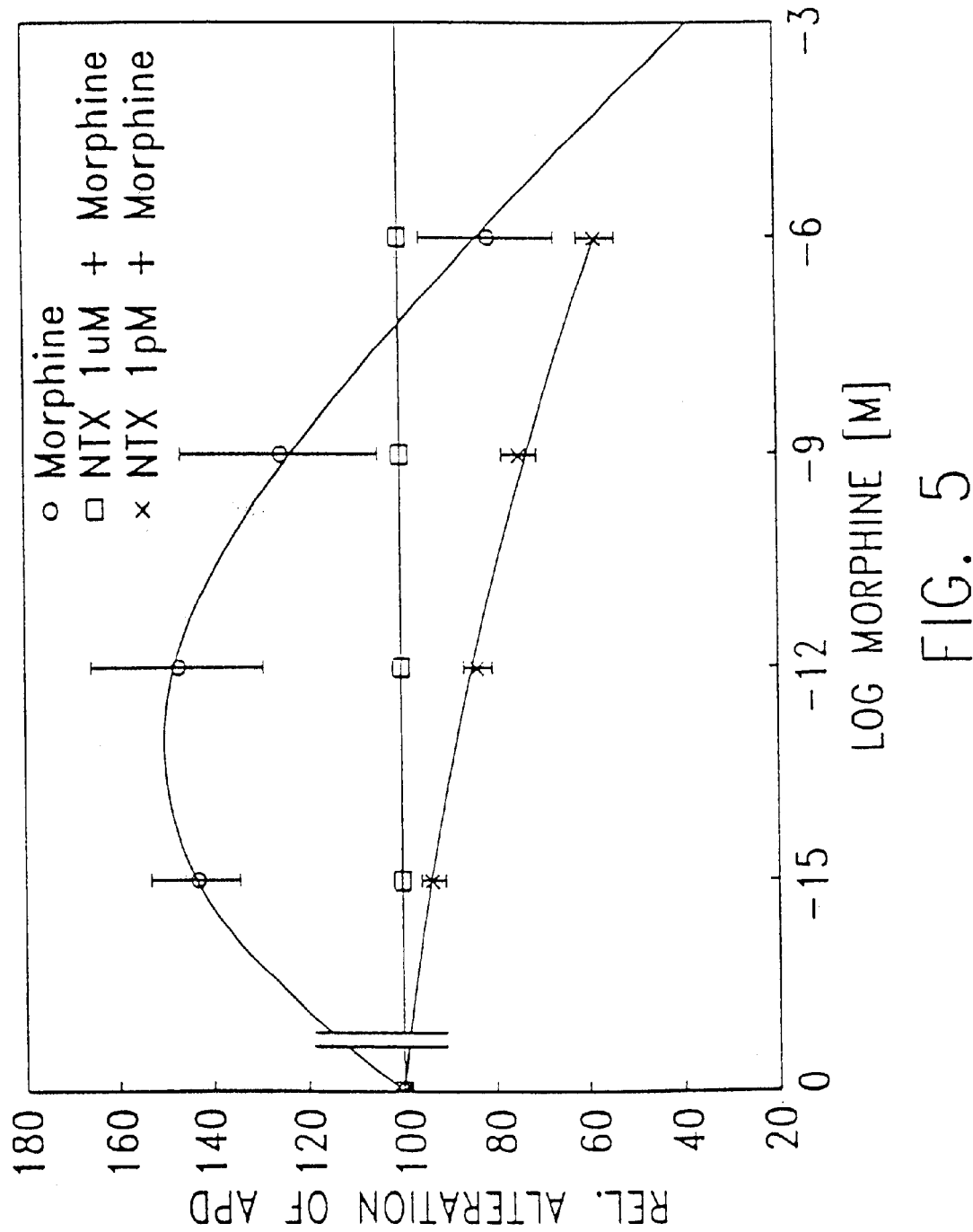
FIG. 5 represents similar selective blocking of excitatory APD-prolonging effects elicited by morphine in DRG neurons when co-administered with a low (pM) concentration of naltrexone, thereby unmasking potent inhibitory APD shortening by low concentrations of morphine. In contrast, a higher ($\mu$M) concentration of naltrexone blocks both inhibitory as well as excitatory opioid effects.

FIG. 5 shows that excitatory APD-prolonging eeffects elicited by morphine in DRG neurons (○) are also selectively blocked by co-administration of a low (pM) concentration of naltrexone (NTX), thereby unmasking-potent dose-dependent inhibitory APD shortening by low concentrations or morphine (X). In contrast, pretreatment with a higher ($\mu$M) concentration of NTX blocks both inhibitory as well as excitatory effects of morphine (□) (similar blockade occurs with 1 nM NTX). These dose-response curves are based on data from 18 neurons, all of which showed only excitatory APD prolongation responses when tested prior to introduction of NTX. The inhibitory potency of morphine in the presence of pM NTX becomes comparable to that of etorphine and dihydroetorphine (see FIG. 3).

EXAMPLE 3
Chronic Co-treatment of DRG Neurons With Morphine and Ultra-low-dose Naloxone or Naltrexone Prevents Development of Opioid Excitatory Supersensitivity ("Dependence") and Tolerance Co-administration of ultra-low (pM) concentrations of naloxone or naltrexone during chronic treatment of DRG neurons with $\mu$M levels of morphine was effective in preventing development of opioid excitatory supersensitivity and tolerance which generally occurs after sustained exposure to bimodally-acting opioids. Acute application of fM dynorphin A-(1–13) or fM morphine (n=21), as well as 1 nM naloxone (n=11), to DRG neurons chronically exposed to 1 $\mu$M morphine together with 1 pM naloxone or naloxone or naltrexone (for 1–10 weeks) did not evoke the usual excitatory APD prolongation observed in chronic morphine-treated cells tested after washout with BSS (see FIG. 6). Furthermore, there was no evidence of tolerance to the usual inhibitory effects of µM opioids (n=6) (FIG. 6).

These results are consonant with previous data that blockade of sustained opioid excitatory effects by cholera toxin-B sub-unit during chronic morphine treatment of DRG neurons prevents development of tolerance and dependence. (see Shen and Crain, *Brain Res.*, Vol. 597, pp. 74–83 (1992)). This toxin sub-unit selectively interferes with GM1 ganglioside regulation of excitatory opioid receptor functions (see Shen and Crain, *Brain Res.*, Vol. 531, pp. 1–7 (1990) and Shen et al., *Brain Res.*, Vol. 559, pp. 130–138 (1991)).

Similarly, in the presence of pM etorphine, chronic µM morphine-treated DRG neurons did not develop signs of tolerance or dependence. FIG. 6 outlines the assay procedure used for testing the effectiveness of these and other antagonists at excitatory opioid receptors in preventing development of tolerance/dependence during chronic co-treatment of DRG neurons with morphine.

EXAMPLE 4
Excitatory Opioid Receptor Antagonists Enhance Analgesic Potency and Reduce Dependence Liability and Other Side Effects of Morphine When Administered in Combination With Morphine Electrophysiological studies on DRG neurons in culture indicated that pretreatment with low fM-pM concentrations of naltrexone, naloxone, diprenorphine, etorphine or dihydroetorphine is remarkably effective in blocking excitatory APD-prolonging effects of morphine or other bimodally-acting opioid agonists by selective antagonist actions at mu, delta and kappa excitatory opioid receptors on these cells. In the presence of these selective excitatory opioid receptor antagonists, morphine and other clinically used bimodally-acting opioid agonists showed markedly increased potency in evoking the inhibitory effects on the action potential of sensory neurons which are generally considered to underlie opioid analgesic action in vivo.

These bimodally-acting opioid agonists became effective in shortening, instead of prolonging, the APD at pM-nM (i.e., $10^{-12}$–$10^{-9}$ M) concentrations, whereas 0.1–1 µM (i.e., $10^{-7}$–$10^{-6}$ M) levels were generally required to shorten the APD (FIGS. 4B and 5). Selective blockade of the excitatory side effects of these bimodally-acting opioid agonists eliminates the attenuation of their inhibitory effectiveness that would otherwise occur. Hence, according to this invention, the combined use of a relatively low dose of one of these selective excitatory opioid receptor antagonists, together with morphine or other bimodally-acting mu, delta or kappa opioid agonists, will markedly enhance the analgesic potency of said opioid agonist, and render said opioid agonist comparable in potency to etorphine or dihydroetorphine, which, when used alone, are >1000 times more potent than morphine in eliciting analgesia.

Co-administration of one of these excitatory opioid receptor antagonists at low (pM) concentration ($10^{-12}$ M) during chronic treatment of sensory neurons with $10^{-6}$ M morphine or other bimodally-acting opioid agonists (>1 week in culture) prevented development of the opioid excitatory supersensitivity, including naloxone-precipitated APD-prolongation, as well as the tolerance to opioid inhibitory effects that generally occurs after chronic opioid exposure. This experimental paradigm was previously utilized by the inventors on sensory neurons in culture to demonstrate that co-administration of $10^{-7}$ M cholera toxin-B sub-unit, which binds selectively to GM1 ganglioside and thereby blocks excitatory GM1-regulated opioid receptor-mediated effects, but not opioid inhibitory effects (see Shen and Crain, *Brain Res.*, Vol. 531, pp. 1–7 (1990)), during chronic opioid treatment prevents development of these plastic changes in neuronal sensitivity that are considered to be cellular manifestations related to opioid dependence/addiction and tolerance in vivo (see Shen and Crain, *Brain Res.*, Vol. 597, pp. 74–83 (1992)).

EXAMPLE 5
Cotreatment of Mice With Morphine Plus Ultra Low Dose Naltrexone Enhances Opioid Antinociceptive Potency Antinociceptive effects of opioids were measured using a warm-water tail flick assay similar to methods described in Horan, P. J., et al. *J. Pharmacol. Exp. Ther.* 264:1446–1454 (1993). In this regard, each mouse was inserted into a plastic restraining device that permitted the tail to be dipped into a water bath maintained at 55° C. The latency to a rapid tail flick was recorded; mice with control latencies >5 seconds were excluded from these tests and a 10 second cutoff was used to minimize tissue damage. Six sequential control tests were made, each with a 10 minute interval. The latencies of the last four tests were averaged to provide a control value. Percent antinociception was calculated according to the formula: 100×[(test latency−control latency)/10−control latency)]. Differences between treatment groups were examined for statistical significance by means of ANOVA with Neuman-Keuls tests.

Figure 7:
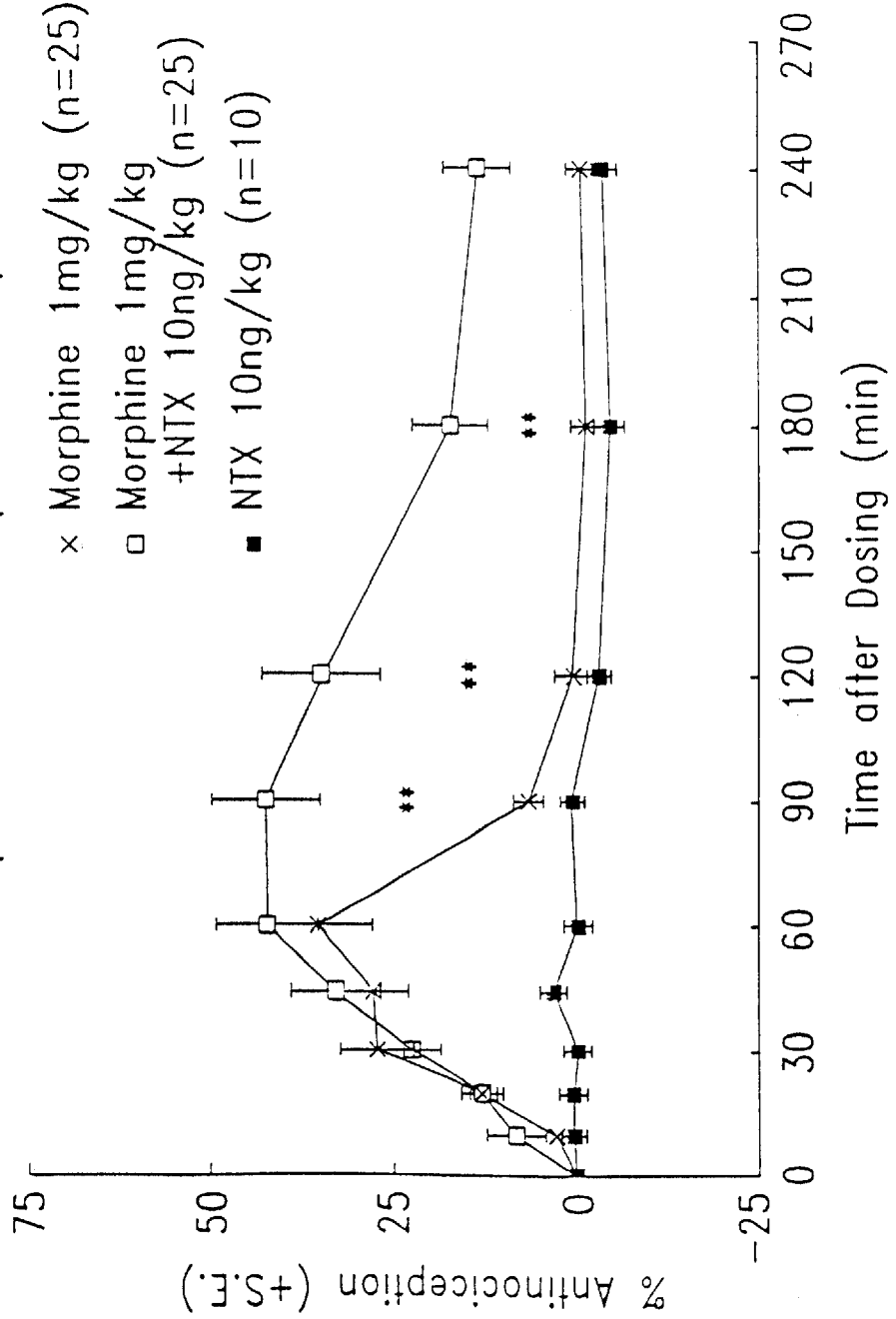
FIG. 7 represents a comparison of the antinociceptive potency of 1 mg/kg morphine administered (i.p.) to mice alone, 10 ng/kg naltrexone administered (i.p.) to mice alone, and a combination of 1 mg/kg morphine and 10 ng/kg naltrexone administered (i.p.) to mice. Shown are the time-response curves for 1 mg/kg morphine (×); 1 mg/kg morphine and 10 ng/kg naltrexone (NTX) (□); 10 ng/kg naltrexone (■), in a warm-water (55° C.) tail-flick test. Twenty-five mice were used per dosing group (10 animals for NTX alone). Injection of 10 ng of NTX per kg alone did not elicit analgesic effects. **, Statistically significant difference between individual morphine vs. morphine plus naltrexone time points: $P<0.01$.

Untreated mice showed tail-flick latencies of 2.15±0.4 seconds (mean±SD; n=58). Cotreatment of mice with 10 mg of morphine per kg plus a 1000-fold lower dose of naltrexone (10 µg/kg, i.p.) resulted in moderate attenuation and no significant enhancement of the analgesic potency of morphine injected alone. In contrast, cotreatment of mice with 1 mg of morphine per kg plus a 100,000 fold lower dose of naltrexone (10 ng/kg, i.p.) demonstrated that in the presence of this extremely low dose of naltrexone, the peak values of tail-flick latencies at 1 hour were maintained during the subsequent hour, whereas the antinociceptive effects of morphine alone rapidly decreased during this same period. Furthermore, a remarkable degree of antinociception was maintained for >1.5 hours after the effects of 1 mg of morphine per kg alone were no longer detectable (n=25; FIG. 7). The marked enhancement of the analgesic potency of morphine in mice during cotreatment with 10 ng of naltrexone per kg is quite consonant with the unmasking of potent inhibitory effects of 1 pM–1 nM morphine in DRG neurons in vitro by cotreatment with 1 pM naltrexone.

EXAMPLE 6
Cotreatment of Mice With Morphine Plus Low-Dose Naltrexone Attenuates Withdrawal Jumping Behavior Acute Physical Dependence Assays Acute physical dependence was assessed by recording naloxone-precipitated withdrawal jumping behavior in mice that had been injected 3–4 hours earlier with a 100 mg/kg (s.c.) dose of morphine (Horan, P. J., et al. supra; Yano, I. and Takemori, A. E. *Res. Commun. Chem. Pathol. Pharmacol.* 16:721–733 (1977); Sofuoglu, M., et al. *J. Pharmacol. Exp. Ther.* 254:841–846 (1990), administered alone or together with a low dose of naltrexone. Each mouse was placed individually in a tall container and the number of abrupt, stereotyped jumps was recorded during a 15 minute period after administration of naloxone (10 mg/kg, i.p.). Differences between treatment groups were examined for statistical significance by means of $X^2$ tests.

Figure 8:
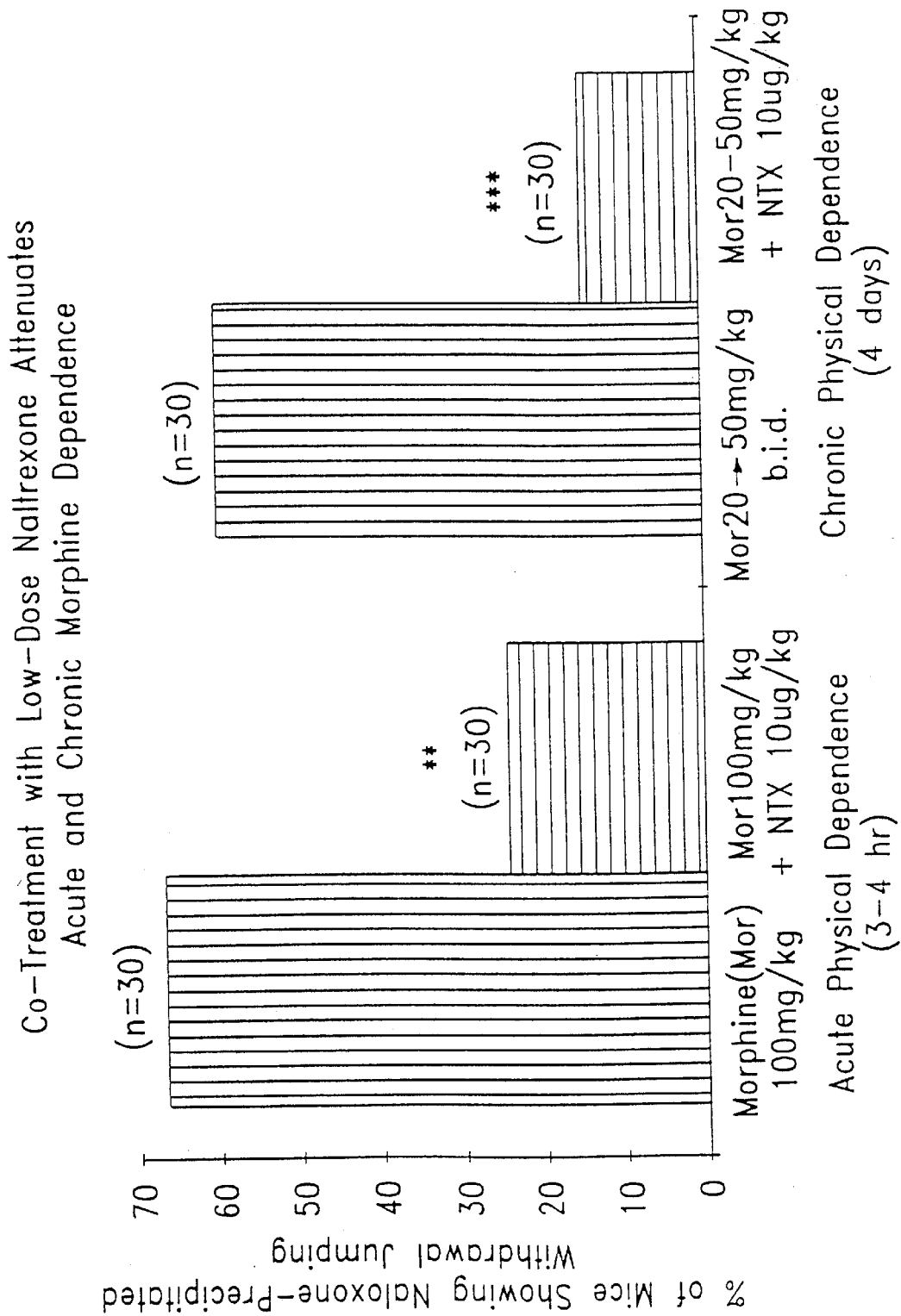
FIG. 8 represents a comparison of the percentage of mice showing naloxone-precipitated withdrawal jumping (i) 3–4 hours after injection with morphine alone (100 mg/kg, s.c.), and morphine (100 mg/kg, s.c.) plus naltrexone (10 $\mu$g/kg, s.c.) (acute physical dependence assay); and (ii) 4 days after increasing daily injections with morphine alone (20–50 mg/kg, s.c.), and morphine (20–50 mg/kg, s.c.) plus naltrexone (10 $\mu$g/kg, s.c.) (chronic physical dependence assay). , Statistically significant difference from control morphine alone group: $P<0.01$; , $P<0.001$.

Three to four hours after the administration of a high dose of morphine (100 mg/kg, s.c.), injection of naloxone (10 mg/kg, i.p.) evoked characteristic withdrawal jumping behavior. About 67% of these treated mice (n=30) showed 5–100 robust jumps during a 15 minute test period (n=30; FIG. 8), whereas jumping behavior was observed in only 10–20% of untreated mice. On the other hand, after cotreatment of mice with a 10,000-fold lower dose of naltrexone (10 µg/kg) administered 15 minutes prior to and together with 100 mg of morphine per kg, the incidence of naloxone-precipitated jumping behavior was markedly reduced to only 23% of the treated animals (n=30); FIG. 8). The mice were routinely pretreated with naltrexone to ensure antagonist binding to excitatory opioid receptors prior to their possible long-lasting activation by morphine. An additional injection of naltrexone (10 µg/kg, s.c.) was made 2 hours after administration of morphine plus naltrexone, because this antagonist has been reported to have a much shorter duration of action in mice, in contrast to humans.

Antinociceptive tail-flick tests on naive mice were made in order to show that this effect of 10 µg of naltrexone per kg was mediated primarily by blocking excitatory, rather than inhibitory, opioid receptor functions. Cotreatment of mice with 100 mg of morphine per kg plus 10 µg of naltrexone per kg (i.p.) did not significantly attenuate the potent (supramaximal) analgesic effect of 100 mg of morphine per kg injected alone. In both groups of treated mice, tail-flick latencies rapidly increased to the peak cutoff value of 10 seconds.

Chronic Physical Dependence and Tolerance Assays

Chronic physical dependence was assessed by similar naloxone-precipitated withdrawal jumping behavior tests as described above in mice that had been injected for four days (twice daily) with increasing doses of morphine (20–50 mg/kg, s.c.), alone or together with a low dose of naltrexone. On the fifth day, the animals were primed with morphine (10 mg/kg) and challenged 1 hour later with naloxone (10 mg/kg, i.p.), as in previous chronic morphine-dependence assays (Sofuoglu, M., et al. *J. Pharmacol. Exp. Ther.* 254:841–846 (1990); Brase, D. B., et al. *J. Pharmacol. Exp. Ther.* 197:317–325 (1976); Way, E. L. and Loh, H. H. *Ann. N.Y. Acad. Sci.* 281:252–261 (1976)). Differences between treatment groups were examined for statistical significance by means of $X^2$ tests.

About 60% of the treated mice showed stereotyped jumping as observed in the acute dependence tests (n=30; FIG. 8). By contrast, after cotreatment of mice with 10 µg of naltrexone per kg (s.c.) administered 15 minutes prior to and together with each of the morphine injections indicated above, naloxone-precipitated jumping occurred in only 13% of the mice (n=30; FIG. 8). Tail-flick assays on naive mice showed that cotreatment with 20 mg of morphine per kg plus 10 µg of naltrexone per kg did not significantly attenuate the analgesic effect of 20 mg of morphine per kg injected alone. In similar-chronic cotreatment tests using a 10-fold lower dose of naltrexone (1 µg/kg), withdrawal jumping was still markedly attenuated from 60% down to 30% of the mice (n=30; data not shown). These results demonstrate that, chronic cotreatment with morphine plus 50,000- to 5,000-fold lower doses of naltrexone significantly decreased development of physical dependence.

Tail-flick assays on some of these chronic cotreated mice at 1 day after drug withdrawal showed that opioid tolerance was also partially attenuated. Acute injection of 1 mg of morphine per kg resulted in a much larger degree of antinociception in chronic morphine plus 10 ng of naltrexone per kg cotreated mice (15%±3%, n=10; time to peak effect at 30 minutes), as compared to chronic morphine-treated mice (3%±2% at 30 minutes, n=10; peak effect of 7%±1$ at 60 minutes) (data not shown).

Figure 9:
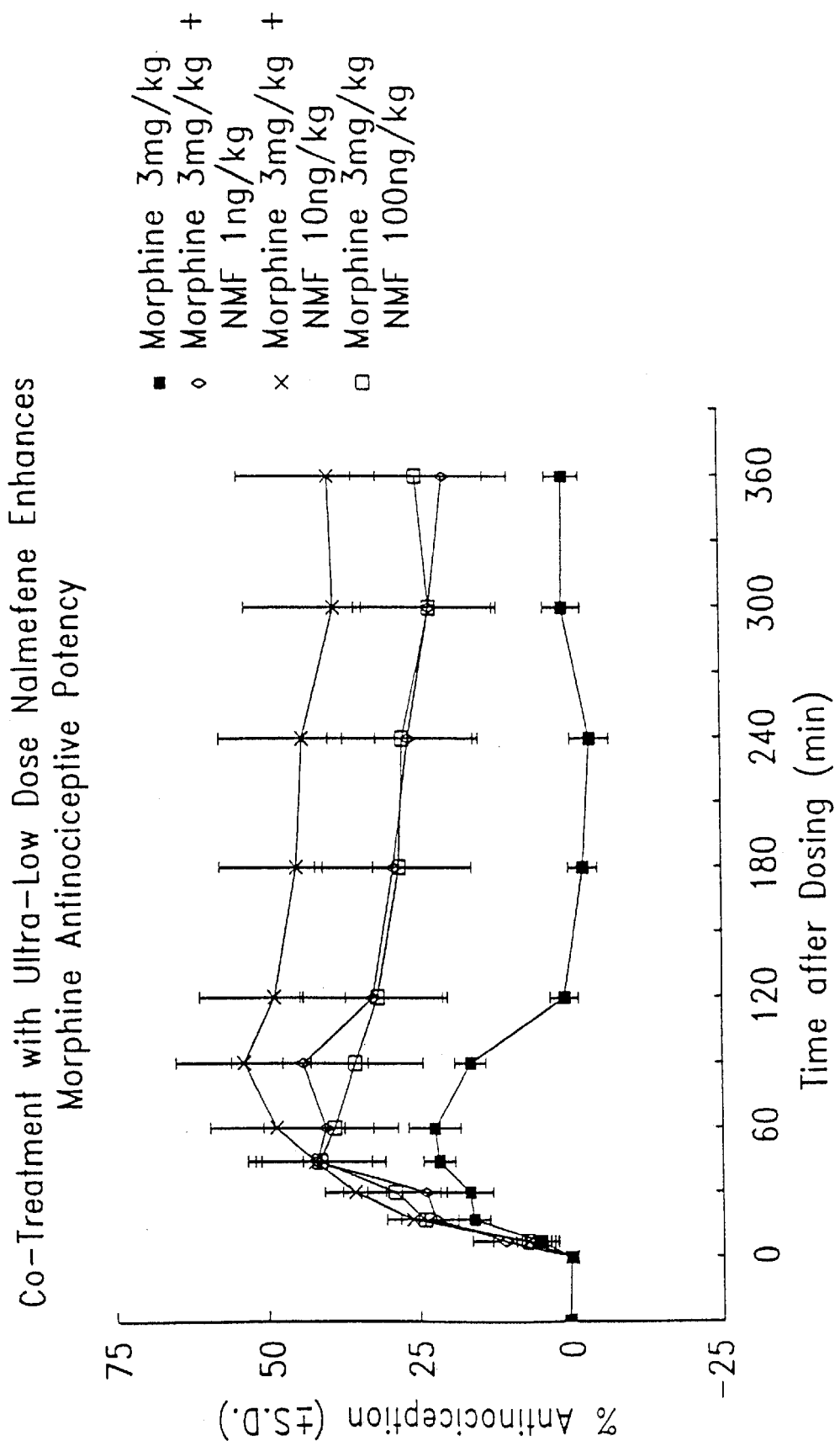
FIG. 9 represents a comparison of the antinociceptive potency of morphine administered (i.p.) to mice alone, and morphine administered (i.p.) to mice in combination with various ultra-low doses of nalmefene (NMF). Shown are the time-response curves for 3 mg/kg morphine (●); 3 mg/kg morphine and 100 ng/kg nalmefene (□); 3 mg/kg morphine and 10 ng/kg nalmefene (×); and 3 mg/kg morphine and 1 ng/kg nalmefene (◇) in a warm-water (55° C.) tail-flick test. Ten mice were used per dosing group.

EXAMPLE 7
Cotreatment of Mice With Morphine Plus Low-Dose Nalmefene Enhances Opioid Antinociceptive Potency Mice were injected (i.p.) with 3 mg/kg morphine alone, and 3 mg/kg morphine in combination with 30,000-fold lower dose of nalmefene (100 ng/kg, i.p.), 300,000-fold lower dose of nalmefene (10 ng/kg, i.p.) and 3,000,000-fold lower dose of nalmefene (1 ng/kg, i.p.). Ten mice were used per dosing group. Antinociceptive effects of opioids were measured using a warm-water tail f-lick assay as described above. The results are presented in FIG. 9. Co-treatment of mice with ultra-low doses of nalmefene (NLF) enhances morphine's antinociceptive potency, in contrast to the characteristic attenuation of morphine analgesia by higher doses of nalmefene. Co-treatment with 1 ng/kg nalmefene was as effective as 10 ng/kg naltrexone in enhancing morphine antinociceptive potency (compare FIGS. 7 and 9).

Figure 10:
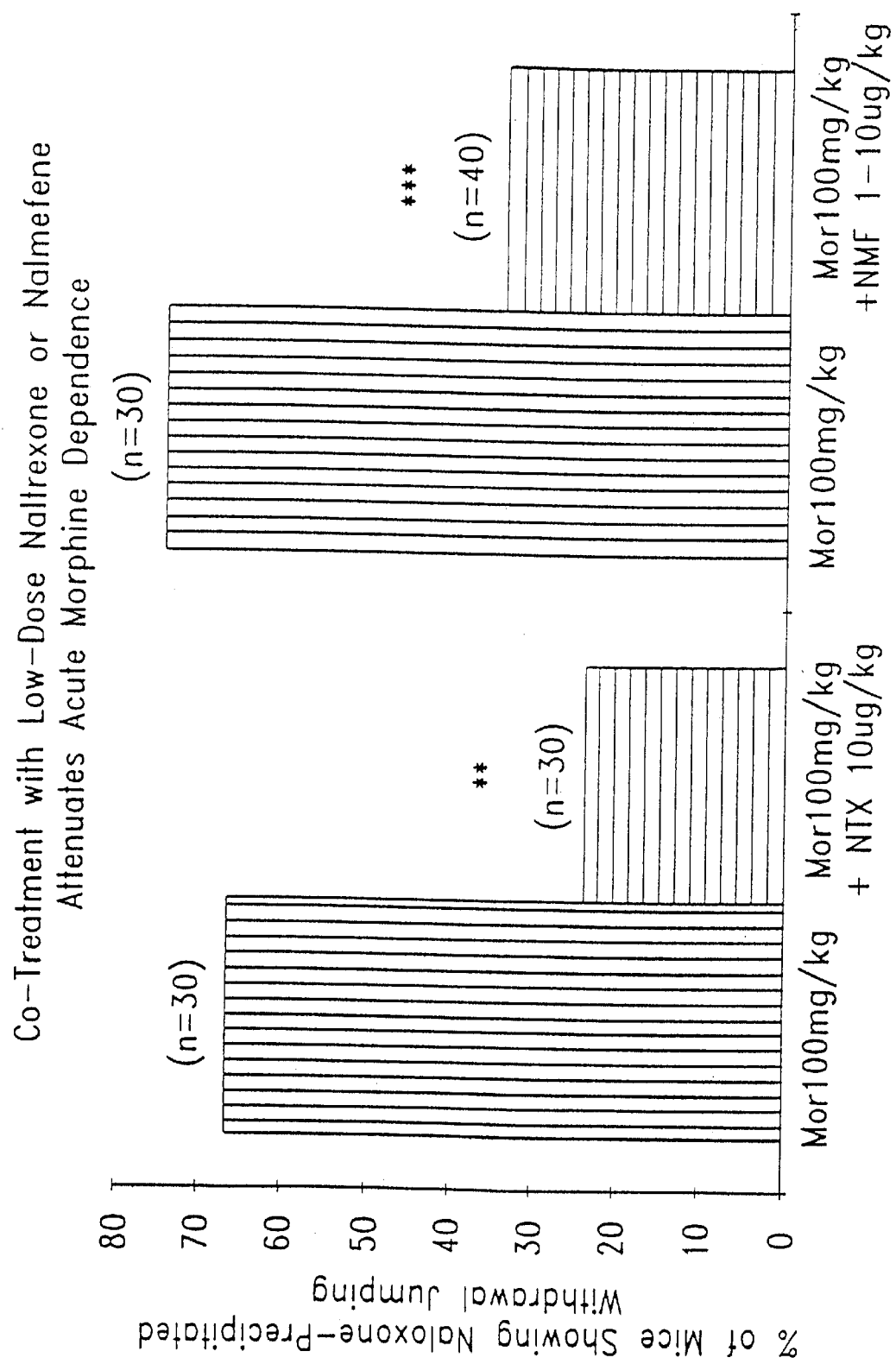
FIG. 10 represents a comparison of the percentage of mice showing naloxone-precipitated withdrawal jumping 4 hours after injection (acute physical dependence assay) with a 100 mg/kg (s.c.) dose of morphine (Mor) alone or in combination with 1 or 10 $\mu$g/kg (s.c.) dose of nalmefene (NMF) or 10 $\mu$g/kg (s.c.) dose of naltrexone (NTX). Additional injections of nalmefene (1 or 10 $\mu$g/kg, s.c.) or naltrexone (10 $\mu$g/kg, s.c.) were made 90 minutes after the initial injections. , Statistically significant difference from control morphine alone group: $P<0.01$; , $P<0.001$.

EXAMPLE 8
Cotreatment of Mice With Morphine Plus Low-Dose Nalmefene Attenuates Withdrawal Jumping Behavior Acute Physical Dependence Assays Mice were injected with a 100 mg/kg (s.c.) dose of morphine, administered either alone or in combination with 1 or 10 µg/kg (s.c.) dose of nalmefene or 10 µg/kg (s.c.) dose of naltrexone (as control), followed by additional injections of nalmefene (1 or 10 µg/kg, s.c.) or naltrexone (10 µg/kg, s.c.) 90 minutes after the initial injections. Acute physical dependence was assessed by recording naloxone-precipitated withdrawal jumping behavior in mice 4 hours after the initial injections. The results are presented in FIG. 10. Co-treatment of mice for 4 hours with morphine plus the low dose nalmefene (NLF; n=40) or naltrexone (NTX; n=30) attenuates naloxone-precipitated withdrawal-jumping in the acute physical dependence assays. These results demonstrate that co-treatment with nalmefene is as effective as naltrexone in attenuating morphine dependence liability. Tests with 1 µg/kg nalmefene (n=10) indicate that nalmefene may even be more effective than naltrexone in attenuating morphine dependence liability.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

What is claimed is:

1. A method for selectively enhancing the analgesic potency of a bimodally-acting opioid agonist and simultaneously attenuating anti-analgesia, hyperalgesia, hyperexcitability, physical dependence and/or tolerance effects associated with the administration of said bimodally-acting opioid agonist, comprising administering to a subject an analgesic or sub-analgesic amount of a bimodally-acting opioid agonist selected from the group consisting of morphine, codeine, fentanyl analogs, buprenorphine, methadone, enkephalins, dynorphins, and endorphins, and an amount of an excitatory opioid receptor antagonist selected from the group consisting of naloxone and naltrexone effective to enhance the analgesic potency of said bimodally-acting opioid agonist and attenuate the anti-analgesia, hyperalgesia, hyperexcitability, physical dependence and/or tolerance effects of said bimodally-acting opioid agonist.

2. The method of claim 1, wherein the amount of the excitatory opioid receptor antagonist administered is at least 100–1000 times less than the amount of the bimodally-acting opioid agonist.

3. The method of claim 1, wherein the bimodally-acting opioid agonist is morphine.

4. The method of claim 1, wherein the bimodally-acting opioid agonist is codeine.

5. The method of claim 1, wherein the bimodally-acting opioid agonist is methadone.

6. The method of claim 1, wherein the excitatory opioid receptor antagonist is naloxone.

7. The method of claim 1, wherein the excitatory opioid receptor antagonist is naltrexone.

8. The method of claim 1, wherein the mode of administration is selected from the group consisting of oral, sublingual, intramuscular, subcutaneous and intravenous administration.

9. A method for treating pain in a subject comprising administering to said subject an analgesic or sub-analgesic amount of a bimodally-acting opioid agonist selected from the group consisting of morphine, codeine, fentanyl analogs, buprenorphine, methadone, enkephalins, dynorphins, and endorphins, and an amount of an excitatory opioid receptor antagonist selected from the group consisting of naloxone and naltrexone effective to enhance the analgesic potency of said bimodally-acting opioid agonist and attenuate the anti-analgesia, hyperalgesia, hyperexcitability, physical dependence and/or tolerance effects of said bimodally-acting opioid agonist.

10. The method of claim 9, wherein the amount of the excitatory opioid receptor antagonist administered is at least 100–1000 times less than the amount of the bimodally-acting opioid agonist.

11. The method of claim 9, wherein the bimodally-acting opioid agonist is morphine.

12. The method of claim 9, wherein the bimodally-acting opioid agonist is codeine.

13. The method of claim 9, wherein the bimodally-acting opioid agonist is methadone.

14. The method of claim 9, wherein the excitatory opioid receptor antagonist is naloxone.

15. The method of claim 9, wherein the excitatory opioid receptor antagonist is naltrexone.

16. The method of claim 9, wherein the mode of administration is selected from the group consisting of oral, sublingual, intramuscular, subcutaneous and intravenous administration.

17. A method for detoxifying and treating an opiate addict comprising administering to the opiate addict an analgesic or sub-analgesic amount of a bimodally-acting opioid agonist selected from the group consisting of morphine, codeine, fentanyl analogs, buprenorphine, methadone, enkephalins, dynorphins, and endorphins, and an amount of an excitatory opioid receptor antagonist selected from the group consisting of naloxone and naltrexone effective to enhance the analgesic potency of said bimodally-acting opioid agonist and attenuate the anti-analgesia, hyperalgesia, hyperexcitability, physical dependence and/or tolerance effects of said bimodally-acting opioid agonist, thereby detoxifying and treating said opiate addict.

18. The method of claim 17, wherein the bimodally-acting opioid agonist is methadone.

19. The method of claim 17, wherein the excitatory opioid receptor antagonist is naltrexone.

20. The method of claim 17, wherein the excitatory opioid receptor antagonist is naloxone.

21. The method of claim 17, wherein the bimodally acting opioid agonist is methadone and the excitatory opioid receptor antagonist is naloxone.

22. The method of claim 17, wherein the bimodally acting opioid agonist is methadone and the excitatory opioid receptor antagonist is naltrexone.

23. The method of claim 17, wherein the mode of administration is selected from the group consisting of oral, sublingual, intramuscular, subcutaneous and intravenous administration.

24. A composition comprising an analgesic or sub-analgesic amount of a bimodally-acting opioid agonist selected from the group consisting of morphine, codeine, fentanyl analogs, buprenorphine, methadone, enkephalins, dynorphins, and endorphins, and an amount of an excitatory opioid receptor antagonist selected from the group consisting of naloxone and naltrexone effective to enhance the analgesic potency of said bimodally-acting opioid agonist and attenuate the anti-analgesia, hyperalgesia, hyperexcitability, physical dependence and/or tolerance effects of said bimodally-acting opioid agonist.

25. The composition of claim 24, wherein the amount of the excitatory opioid receptor antagonist administered is at least 100–1000 times less than the amount of the bimodally-acting opioid agonist.

26. The composition of claim 24, wherein the bimodally-acting opioid agonist is morphine.

27. The composition of claim 24, wherein the bimodally-acting opioid agonist is codeine.

28. The composition of claim 24, wherein the bimodally-acting opioid agonist is methadone.

29. The composition of claim 24, wherein the excitatory opioid receptor antagonist is naloxone.

30. The composition of claim 24, wherein the excitatory opioid receptor antagonist is naltrexone.

31. A method for selectively enhancing the analgesic potency of a bimodally-acting opioid agonist and simultaneously attenuating anti-analgesia, hyperalgesia, hyperexcitability, physical dependence and/or tolerance effects associated with the administration of said bimodally-acting opioid agonist, comprising administering to a subject an analgesic or sub-analgesic amount of a bimodally-acting opioid agonist selected from the group consisting of morphine, codeine, fentanyl analogs, buprenorphine, methadone, enkephalins, dynorphins, and endorphins, and an amount of an excitatory opioid receptor antagonist effective to enhance the analgesic potency of said bimodally-acting opioid agonist and attenuate the anti-analgesia, hyperalgesia, hyperexcitability, physical dependence and/or tolerance effects of said bimodally-acting opioid agonist.

* * * * *

(12) EX PARTE REEXAMINATION CERTIFICATE (5251st)
United States Patent
Crain et al.

(10) Number: US 6,362,194 C1
(45) Certificate Issued: *Jan. 3, 2006

(54) METHOD AND SIMULTANEOUSLY ENHANCING ANALGESIC POTENCY AND ATTENUATING DEPENDENCE LIABILITY CAUSED BY MORPHINE AND OTHER BIMODALLY-ACTING OPIOID AGONISTS

(75) Inventors: Stanley M. Crain, Leonia, NJ (US); Ke-fei Shen, Flushing, NY (US)

(73) Assignee: Albert Einstein College of Medicine of Yeshiva University, a division of Yeshiva University, Bronx, NY (US)

Reexamination Request:
No. 90/006,475, Dec. 2, 2002

Reexamination Certificate for:
Patent No.: 6,362,194
Issued: Mar. 26, 2002
Appl. No.: 09/585,517
Filed: Jun. 1, 2000

( * ) Notice: This patent is subject to a terminal disclaimer.

Related U.S. Application Data

(63) Continuation of application No. 09/094,977, filed on Jun. 16, 1998, now Pat. No. 6,096,756, which is a continuation of application No. 08/759,590, filed on Dec. 3, 1996, now Pat. No. 5,767,125, which is a continuation of application No. 08/552,296, filed on Nov. 3, 1995, now Pat. No. 5,580,876, which is a continuation-in-part of application No. 08/276,966, filed on Jul. 19, 1994, now Pat. No. 5,512,578, which is a continuation-in-part of application No. 08/097,460, filed on Jul. 27, 1993, now Pat. No. 5,472,943, which is a continuation-in-part of application No. 07/947,690, filed on Sep. 21, 1992, now abandoned.

(51) Int. Cl.
*A01N 43/42* (2006.01)

(52) U.S. Cl. .................................................. 514/285
(58) Field of Classification Search .................. 514/285
See application file for complete search history.

(56) References Cited

U.S. PATENT DOCUMENTS

| | | |
|---|---|---|
| 3,493,657 A | 2/1970 | Lewenstein et al. |
| 3,773,955 A | 11/1973 | Pachter et al. |
| 3,879,555 A | 4/1975 | Pachter et al. |
| 4,457,933 A | 7/1984 | Gordon et al. |
| 4,582,835 A | 4/1986 | Lewis et al. |

OTHER PUBLICATIONS

Gan, et al., Anesthesiology, 87:1075–81, 1997.
Joshi, et al., Anesthesiology, 90:1007–11, 1999.
Cepeda, et al., Pain, 107:41–46, 2004.
Schmidt et al., 1985, "Postoperative pain relief with naloxone. Severe respiratory depression and pain after high dose buprenorphine," Anaesthesia 40:583–586.
Pedersen et al., 1985, "Naloxone—a strong analgesic in combination with high dose buprenorphine," Brit. J. Anaesth. 57: 1045–1046.
Bergman et al., 1988, "Low dose naloxone enhances buprenorphine in a tooth pulp antinociceptive assay," Arch. Int. Pharmacodyn. Ther. 291:229–37.
Dum and Herz, 1981, "In vivo Receptor Binding of the Opiate Partial Agonist, Buprenorphine, Correlated with its Agonistic and Antagonistic Actions," Br. J. Pharmac. 74:627–633.
Vaccarino et al., 1989, "Analgesia produced by normal doses of opioid antagonists alone and in combination with morphine," Pain 36:103–09.
Levine et al., 1988, "Potentiation of pentazocine and analgesia by low–dose naloxone," J. Clin. Invest. 82(5):1574–77.
Specification of U.S. Pat. No. Re. 36,547, (Mar. 2002).
Crain & Shen, 1995, Ultra–low concentrations of naloxone selectively antagonize excitatory effects of morphine on sensory neurons, thereby increasing its antinociceptive potency and attenuating tolerance/dependence during chronic co–treatment. Proc Natl Acad Sci U S A. 1995 Nov. 7; 92(23):10540–10544.

*Primary Examiner*—Raymond J Henley, III

(57) ABSTRACT

This invention relates to a method for selectively enhancing the analgesic potency of a bimodally-acting opioid agonist such as morphine and simultaneously attenuating anti-analgesia, hyperalgesia, hyperexcitability, physical dependence and/or tolerance effects associated with the administration of the bimodally-acting opioid agonist. The method of the present invention comprises administering to a subject an analgesic or sub-analgesic amount of a bimodally-acting opioid agonist such as morphine and an amount of an excitatory opioid receptor antagonist such as naltrexone or nalmefene efective to enhance the analgesic potency of the bimodally-acting opioid agonist and attenuate the anti-analgesia, hyperalgesia, hyperexcitability, physical dependence and/or tolerance effects of the bimodally-acting opioid agonist.

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 1, lines 9–21:

This is a continuation of application Ser. No. 09/094,977, filed Jun. 16, 1998, now U.S. Pat. No. 6,096,756, which is a continuation of application Ser. No. 08/759,590, filed Dec. 3, 1996, now U.S. Pat. No. 5,767,125, which is a *continuation of application Ser. No. 08/552,296, filed Nov. 3, 1995, now U.S. Pat. No. 5,580,876, issued Dec. 3, 1996, which is* a continuation-in-part of application Ser. No. 08/276,966, filed Jul. 19, 1994, which issued as U.S. Pat. No. 5,512,578 and reissued as U.S. Reissue Pat. No. 36,547, which is a continuation-in-part of application Ser. No. 08/097,460, filed Jul. 27, 1993, now U.S. Pat. No. 5,472,943, which is a continuation-in-part of application Ser. No. 07/947,690, filed Sep. [19] *21*, 1992, now abandoned, the contents of which are hereby incorporated by reference in their entirety.

AS A RESULT OF REEXAMINATION, IT HAS BEEN DETERMINED THAT:

The patentability of claims 1–23 and 31 is confirmed.

Claims 24–30 are cancelled.

New claims 32–68 are added and determined to be patentable.

*32. The method of claim 3, 4, 5, 6, 7, 8, 11, 12, 13, 14, 15, 16, 17, 18, 19, 20, 21, 22, 23 or 31 wherein the amount of the excitatory opioid receptor antagonist is at least 100–1000 fold less than the amount of the bimodally-acting opioid agonist administered.*

*33. The method of claim 1, 3, 4, 5, 6, 7, 8, 9, 11, 12, 13, 14, 15, 16, 17, 18, 19, 20, 21, 22, 23 or 31 wherein the amount of the excitatory opioid receptor antagonist is 100–1000 fold less than the amount of the bimodally-acting opioid agonist administered.*

*34. The method of claim 1, 3, 4, 5, 6, 7, 8, 9, 11, 12, 13, 14, 15, 16, 17, 18, 19, 20, 21, 22, 23 or 31 wherein the amount of the excitatory opioid receptor antagonist is 1000–10,000,000 fold less than the amount of the bimodally-acting opioid agonist administered.*

*35. The method of claim 1, 3, 4, 5, 6, 7, 8, 9, 11, 12, 13, 14, 15, 16, 17, 18, 19, 20, 21, 22, 23 or 31 wherein the amount of the excitatory opioid receptor antagonist is 10,000–1,000,000 fold less than the amount of the bimodally-acting opioid agonist administered.*

*36. The method of claim 1, 2, 3, 4, 5, 6, 7, 8, 9, 10, 11, 12, 13, 14, 15, 16, 17, 18, 19, 20, 21, 22, 23 or 31 wherein the amount of the bimodally-acting opioid agonist administered is an analgesic amount.*

*37. The method of claim 1, 2, 3, 4, 5, 6, 7, 8, 9, 10, 11, 12, 13, 14, 15, 16, 17, 18, 19, 20, 21, 22, 23 or 31 wherein the amount of the bimodally-acting opioid agonist administered is a sub-analgesic amount.*

*38. The method of claim 32 wherein the amount of the bimodally-acting opioid agonist administered is an analgesic amount.*

*39. The method of claim 32 wherein the amount of the bimodally-acting opioid agonist administered is a sub-analgesic amount.*

*40. The method of claim 33 wherein the amount of the bimodally-acting opioid agonist administered is an analgesic amount.*

*41. The method of claim 33 wherein the amount of the bimodally-acting opioid agonist administered is a sub-analgesic amount.*

*42. The method of claim 34 wherein the amount of the bimodally-acting opioid agonist administered is an analgesic amount.*

*43. The method of claim 34 wherein the amount of the bimodally-acting opioid agonist administered is a sub-analgesic amount.*

*44. The method of claim 35 wherein the amount of the bimodally-acting opioid agonist administered is an analgesic amount.*

*45. The method of claim 35 wherein the amount of the bimodally-acting opioid agonist administered is a sub-analgesic amount.*

*46. The composition of claim 24, 26, 27, 28, 29 or 30 wherein the amount of the excitatory opioid receptor antagonist is 1000–10,000,000 fold less than the amount of the bimodally-acting opioid agonist.*

*47. The composition of claim 24, 26, 27, 28, 29 or 30 wherein the amount of the excitatory opioid receptor antagonist is 10,000–1,000,000 fold less than the amount of the bimodally-acting opioid agonist.*

*48. The composition of claim 24, 25, 26, 27, 28, 29 or 30 wherein the amount of the bimodally-acting opioid agonist is a sub-analgesic amount.*

*49. The composition of claim 46 wherein the amount of the bimodally-acting opioid agonist is an analgesic amount.*

*50. The composition of claim 46 wherein the amount of the bimodally-acting opioid agonist is a sub-analgesic amount.*

*51. The composition of claim 47 wherein the amount of the bimodally-acting opioid agonist is an analgesic amount.*

*52. The composition of claim 47 wherein the amount of the bimodally-acting opioid agonist is a sub-analgesic amount.*

*53. The method of claim 3, 4, 5, 6, 7, 11, 12, 13, 14, 15, 18, 19, 20, 21, 22 and 31, wherein the mode of administration is selected from the group consisting of oral, sublingual, intramuscular, subcutaneous and intravenous administration.*

*54. A composition comprising an analgesic or sub-analgesic amount of a bimodally-acting opioid agonist selected from the group consisting of morphine, codeine, fentanyl analogs, buprenorphine, methadone, enkephalins, dynorphins, and endorphins, and an amount of an excitatory opioid receptor antagonist selected from the group consisting of naloxone and naltrexone effective to enhance the analgesic potency of said bimodally-acting opioid agonist and attenuate the anti-analgesia, hyperalgesia, hyperexcitability, physical dependence and/or tolerance effects of said bimodally-acting opioid agonist, wherein said composition has a greater analgesic potency than said bimodally-acting opioid agonist alone.*

55. The composition of claim 54, wherein the amount of the excitatory opioid receptor antagonist administered is at least 100–1000 times less than the amount of the bimodally-acting opioid agonist.

56. The composition of claim 54, wherein the bimodally-acting opioid agonist is morphine.

57. The composition of claim 54, wherein the bimodally-acting opioid agonist is codeine.

58. The composition of claim 54, wherein the bimodally-acting opioid agonist is methadone.

59. The composition of claim 54, wherein the excitatory opioid receptor antagonist is naloxone.

60. The composition of claim 54, wherein the excitatory opioid receptor antagonist is naltrexone.

61. The composition of claim 56, 57, 58, 59 or 60, wherein the amount of the excitatory opioid receptor antagonist is at least 100–1000 times less than the amount of the bimodally-acting opioid agonist.

62. The composition of claim 54, 56, 57, 58, 59 or 60, wherein the amount of the excitatory opioid receptor antagonist is 100–1000 times less than the amount of the bimodally-acting opioid agonist.

63. The composition of claim 54, 55, 56, 57, 58, 59 or 60, wherein the amount of the bimodally-acting opioid agonist is an analgesic amount.

64. The composition of claim 61, wherein the amount of the bimodally-acting opioid agonist is an analgesic amount.

65. The composition of claim 62, wherein the amount of the bimodally-acting opioid agonist is an analgesic amount.

66. The composition of claim 54, 55, 56, 57, 58, 59 or 60, which is formulated for oral, sublingual, intramuscular, subcutaneous or intravenous administration.

67. The composition of claim 66, which is formulated for oral administration.

68. The composition of claim 24, 25, 26, 27, 28, 29 or 30, which is formulated for oral administration.

* * * * *